United States Patent
Kwon et al.

(10) Patent No.: US 10,688,144 B2
(45) Date of Patent: Jun. 23, 2020

(54) **COMPOSITION FOR PREVENTING OR TREATING OSTEOARTHRITIS CONTAINING AN EXTRACT OF *ANGELICA GIGAS* NAKAI**

(71) Applicant: Kang Hyun Lee, Seoul (KR)

(72) Inventors: Jin-Hwan Kwon, Ansan (KR); Min-Seok Han, Suwon (KR)

(73) Assignee: Kang Hyun Lee, Seoul (KR)

( * ) Notice: Subject to any disclaimer, the term of this patent is extended or adjusted under 35 U.S.C. 154(b) by 252 days.

(21) Appl. No.: 15/421,571

(22) Filed: Feb. 1, 2017

(65) Prior Publication Data

US 2017/0258859 A1    Sep. 14, 2017

(30) Foreign Application Priority Data

Feb. 1, 2016 (KR) .................. 10-2016-0012543

(51) Int. Cl.
| | | |
|---|---|---|
| *A61K 36/00* | (2006.01) | |
| *A61K 36/23* | (2006.01) | |
| *A61K 36/232* | (2006.01) | |
| *A61K 36/234* | (2006.01) | |

(52) U.S. Cl.
CPC .......... *A61K 36/232* (2013.01); *A61K 36/234* (2013.01); *A61K 2236/33* (2013.01)

(58) Field of Classification Search
None
See application file for complete search history.

(56) References Cited

U.S. PATENT DOCUMENTS

2003/0143290 A1* 7/2003 Cho ...................... A61K 36/00
                                                              424/728

FOREIGN PATENT DOCUMENTS

| JP | 2011251934 A | * | 12/2011 |
|---|---|---|---|
| KR | 10-2008-0105825 | | 12/2008 |
| KR | 10-2013-0089305 | | 8/2013 |
| KR | 2013089305 A | * | 8/2013 |
| KR | 10-1319866 | | 10/2013 |
| KR | 10-1497276 | | 2/2015 |

OTHER PUBLICATIONS

Je Byung-sun, "The Study on the Effects of Dang-gui-cheon-gung-tang-ka-mi-bang on the Arthritis", Dept. of Oriental Medicine, Graduate School, Daejeon University, Feb. 2005.
Jin-Hwan Kwon, et al., "Effect of Angelica gigas extract powder on progress of osteoarthritis induced by monosodium iodoacetate in rats", Analytical Science & Technology, vol. 28, No. 1, pp. 72-77, Feb. 2015.
Jin-Hwan Kwon, et al., "Inhibitory effect of Angelica gigas extract powder on induced inflammatory cytokines in rats osteoarthritis", Analytical Science & Technology, vol. 28, No. 4, pp. 260-269, Aug. 2015.
Jin-Hwan Kwon, et al., "Regulatory mechanism of Angelica Gigas extract powder on matrix metalloproteinases in vitro and in vivo model", Analytical Science & Technology, vol. 28, No. 6, pp. 361-369, Dec. 2015.

* cited by examiner

*Primary Examiner* — Michael Barker
*Assistant Examiner* — Randall Winston
(74) *Attorney, Agent, or Firm* — Lex IP Meister, PLLC

(57) ABSTRACT

Provided are a pharmaceutical composition for preventing and/or treating osteoarthritis comprising an extract of *Angelica gigas* Nakai, a pharmaceutical composition for preventing and/or treating osteoarthritis comprising a mixed extract of *Angelica gigas* Nakai and *Cnidium officinale*, and a method of preventing and/or treating osteoarthritis comprising administering the extract of *Angelica gigas* Nakai or the mixed extract of *Angelica gigas* Nakai and *Cnidium officinale*.

6 Claims, 20 Drawing Sheets

Specification includes a Sequence Listing.

FIG. 11

| Group | Body Weights (g) | | | | | |
|---|---|---|---|---|---|---|
| | 0 | 4 | 8 | 12 | 16 | 20 days |
| Normal (n=10) | 205 ± 11 | 232 ± 9 | 266 ± 12 | 291 ± 14 | 316 ± 15 | 341 ± 19 |
| Control (n=10) | 204 ± 8 | 227 ± 8 | 261 ± 11 | 273 ± 10★ | 290 ± 16★ | 315 ± 14★ |
| Treated (n=10) | 206 ± 9 | 230 ± 9 | 266 ± 10 | 284 ± 13 | 301 ± 12# | 329 ± 17# |

Normal: saline injected and treated with saline. Control: MIA injected and treated with distilled water. Treated: MIA injected and treated with Angelica gigas.
★: Statistically significant compared with normal group (★: $p < 0.05$)
: Statistically significant compared with control group (#: $p < 0.05$)

COMPOSITION FOR PREVENTING OR TREATING OSTEOARTHRITIS CONTAINING AN EXTRACT OF *ANGELICA GIGAS* NAKAI

CROSS-REFERENCE TO RELATED APPLICATIONS

This application claims the benefit of Korea Patent Application No. 10-2016-0012543 filed on Feb. 1, 2016 with the Korea Industrial Property Office, the entire disclosure of which is hereby incorporated by reference.

BACKGROUND OF THE INVENTION

1. Field of the Invention

Provided are a pharmaceutical composition for preventing and/or treating osteoarthritis comprising an extract of *Angelica gigas* Nakai, a pharmaceutical composition for preventing and/or treating osteoarthritis comprising a mixed extract of *Angelica gigas* Nakai and *Cnidium officinale*, and a method of preventing and/or treating osteoarthritis comprising administering an extract of *Angelica gigas* Nakai or a mixed extract of *Angelica gigas* Nakai and *Cnidium officinale*.

2. Description of the Related Art

Osteoarthritis is a chronic degenerative disease accompanied by inflammation and pain which are caused by gradual damage of the articular cartilage due to changes in the extracellular matrix constituting the articular cartilage. Osteoarthritis mainly occurs in middle-aged or elderly people, and prevalence of osteoarthritis in Korean people aged 50 years or older is about 40%. The prevalence of osteoarthritis is higher in women than in men as the age increases. Osteoarthritis is caused by a variety of reasons including degenerative changes, immune system disorders, infection, trauma, metabolic disorders, etc. The known factors associated with occurrence of osteoarthritis include nitric oxide (NO), cytokines, proteolytic enzymes, etc.

Further, osteoarthritis is a disease accompanied by gradual loss of articular cartilage in the local joint and secondary changes and symptoms associated therewith, in addition to inflammation. Damage of articular cartilage is initiated by a number of mechanical stimuli, enzymatic reactions due to inflammation, metabolic changes, etc., and damaged articular cartilage becomes very weak to additional damage due to lowered water retention capability by reduction in content of proteoglycan (PG) and length of glycosaminoglycan (GAG) chains. In a process of cartilage destruction causing osteoarthritis, inflammation may be partially induced and lead to the release of inflammation-associated enzymes, thus accelerating the deterioration of cartilage. As osteoarthritis progresses, cartilage is destroyed with the inflammatory response, and PG is released into the synovial fluid to increase concentrations of prostaglandin E2 (PGE2), causing pain. Further, excess NO is generated at inflammation sites and stimulates the necrosis of cellular tissues. With progression of osteoarthritis, articular cartilage loses PG and GAG, and mechanical properties of the articular cartilage such as elasticity and compressive force are changed, which causes changes in the joint capsule and joint fluid, resulting in disorders in lubrication, elimination of metabolites by catabolism, and nutrition of the joint surface.

That is, in the treatment of osteoarthritis, it is important not only to treat inflammation but also to maintain mechanical properties of the cartilage by preventing destruction and/or loss of PG and GAG in the joint.

Accordingly, there is a demand for a novel therapeutic agent for osteoarthritis having effects of treating inflammation and preventing destruction and/or loss of PG and GAG in the joint.

SUMMARY OF THE INVENTION

An embodiment provides a pharmaceutical composition for preventing and/or treating osteoarthritis, comprising an extract of *Angelica gigas* Nakai as an active ingredient.

Another embodiment provides a method of preventing and/or treating osteoarthritis, comprising administering a pharmaceutically effective amount of an extract of *Angelica gigas* Nakai to a subject in need of prevention and/or treatment of osteoarthritis.

Another embodiment provides a pharmaceutical composition for preventing and/or treating osteoarthritis, comprising a mixed extract of *Angelica gigas* Nakai and *Cnidium officinale* as an active ingredient. Another embodiment provides a method of preventing and/or treating osteoarthritis, comprising administering a pharmaceutically effective amount of a mixed extract of *Angelica gigas* Nakai and *Cnidium officinale* to a subject in need of prevention and/or treatment of osteoarthritis. The mixed extract of *Angelica gigas* Nakai and *Cnidium officinale* may be a mixture of *Angelica gigas* Nakai extract and *Cnidium officinale* extract, an extract of a mixture of *Angelica gigas* Nakai and *Cnidium officinale*, or a combination thereof.

Another embodiment provides a health functional food for improving osteoarthritis, comprising an extract of *Angelica gigas* Nakai.

Another embodiment provides a health functional food for improving osteoarthritis, comprising a mixed extract of *Angelica gigas* Nakai and *Cnidium officinale* as an active ingredient. The mixed extract of *Angelica gigas* Nakai and *Cnidium officinale* may be a mixture of *Angelica gigas* Nakai extract and *Cnidium officinale* extract, an extract of a mixture of *Angelica gigas* Nakai and *Cnidium officinale*, or a combination thereof.

Another embodiment provides a method of preparing a composition having effects of preventing, treating, and/or improving osteoarthritis, comprising a step of preparing the extract of *Angelica gigas* Nakai.

Another embodiment provides a method of preparing a composition having effects of preventing, treating, and/or improving osteoarthritis, comprising a step of preparing the mixed extract of *Angelica gigas* Nakai and *Cnidium officinale*.

BRIEF DESCRIPTION OF THE DRAWINGS

FIG. 11 is the result showing changes in the body weight of experimental animals according to treatment periods, after treatment of the *Angelica gigas* Nakai extract;

DETAILED DESCRIPTION

Figure 1:
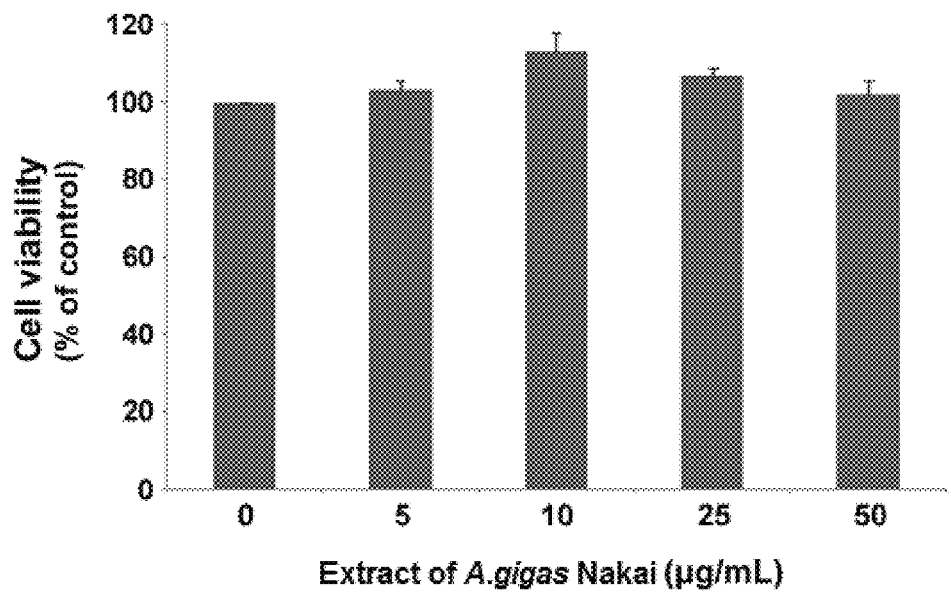
FIG. 1 is a graph showing cell viability according to concentrations of an *Angelica gigas* Nakai extract, after rabbit chondrocytes were treated with an *Angelica gigas* Nakai extract, and then cultured for 24 hours.

The present inventors treated an extract of *Angelica gigas* Nakai to rabbit cartilage tissue cells and white rats with MIA (monosodium iodoacetate)-induced osteoarthritis, and then they measured production amounts of inflammatory mediators, NO, iNOS, and COX-2, and expression and secretion levels of inflammatory cytokines, TNF-α, IL-1β and IL-6. As a result, they found that NO production, and expression and secretion of inflammatory factors were greatly suppressed, and destruction and/or loss of proteoglycan (PG) and glycosaminoglycan (GAG) in the joint was/were significantly inhibited, suggesting use of the extract of *Angelica gigas* Nakai in the prevention, treatment, and/or improvement of osteoarthritis.

Further, the present inventors found that a mixed extract of *Angelica gigas* Nakai and *Cnidium officinale* shows a synergistic effect on the prevention, treatment, and/or improvement of osteoarthritis, suggesting use of the mixed extract of *Angelica gigas* Nakai and *Cnidium officinale* in the prevention, treatment, and/or improvement of osteoarthritis.

*Angelica gigas* is a perennial herbaceous plant belonging to the family Umbelliferae, and mainly cultivated in Korea, Japan, and China for medicinal purposes. Based on its area of distribution, *Angelica gigas* is classified into *Angelica gigas* Nakai produced in Korea, *Angelica acutiloba* Kitagaw produced in Japan, and *Angelica sinensis* Diels produced in china. It known that their ingredients and pharmacological effects are different from each other. Traditionally, the young sprouts of *Angelica gigas* are used as a vegetable side dish, and the roots thereof are used as medicines for various diseases, such as analgesia, anti-cancer, reduction of nephrotoxicity, improvement of liver function, treatment of diabetic hypertension, improvement of blood circulation, etc.

The present disclosure relates to effects of the extract of *Angelica gigas* Nakai in the prevention, treatment, and/or improvement of osteoarthritis.

*Cnidium officinale* originates in China, and is a perennial herbaceous plant distributed in the areas of Korea, Japan, etc. The young sprouts thereof are used as a vegetable side dish, and the roots thereof are used for the treatment of impotence, epilepsy, vaginal discharge, and wind syndrome, and used as a warming agent, a sedative, an analgesic, an invigorant, etc. *Cnidium officinale*, used as an herbal medicine, has a rhizome shaped in a mass of roots.

The 'treatment', as used herein, may be intended to include alleviation or improvement of symptoms, reduction of the extent of disease, delay or alleviation of disease progression, improvement, alleviation or stabilization of the disease state or symptom, partial or complete recovery, extension of survival, other beneficial treatments, etc.

First, an embodiment provides a pharmaceutical composition for preventing and/or treating osteoarthritis, comprising an extract of *Angelica gigas* Nakai as an active ingredient. Another embodiment provides a method of preventing and/or treating osteoarthritis, comprising administering a pharmaceutically effective amount of the extract of *Angelica gigas* Nakai to a subject in need of prevention and/or treatment of osteoarthritis. Still another embodiment provides a pharmaceutical composition for preventing and/or treating osteoarthritis, comprising a mixed extract of *Angelica gigas* Nakai and *Cnidium officinale* as an active ingredient. Still another embodiment provides a method of preventing and/or treating osteoarthritis, comprising administering a pharmaceutically effective amount of the mixed extract of *Angelica gigas* Nakai and *Cnidium officinale* to a subject in need of prevention and/or treatment of osteoarthritis. The method of preventing and/or treating osteoarthritis may further comprise a step of identifying the subject in need of prevention and/or treatment of osteoarthritis, prior to the administration.

The extract of *Angelica gigas* Nakai may be obtained by extracting *Angelica gigas* Nakai (root) with one or more extraction solvents selected from the group consisting of water and linear or branched alcohol having 1 to 4 carbon atoms. For example, the extract of *Angelica gigas* Nakai may be an extract of 90 to 100% (v/v), 92 to 100% (v/v), 96 to 100% (v/v), or 98 to 100% (v/v) ethanol aqueous solution (e.g., 98% (v/v) ethanol aqueous solution) of *Angelica gigas* Nakai (e.g., root). Further, the extract of *Angelica gigas* Nakai may be extracted at 10 to 80° C., 10 to 70° C., 10 to 60° C., 10 to 50° C., 20 to 80° C., 20 to 70° C., 20 to 60° C., 20 to 50° C., 30 to 80° C., 30 to 70° C., 30 to 60° C., 30 to 50° C., 40 to 80° C., 40 to 70° C., 40 to 60° C., or 40 to 50° C.

The extract of *Angelica gigas* Nakai used herein, for example, ethanol extract of *Angelica gigas* Nakai (extracted with 90 to 100% (v/v), 92 to 100% (v/v), 96 to 100% (v/v), or 98 to 100% (v/v) ethanol aqueous solution at 10 to 80° C., 10 to 70° C., 10 to 60° C., 10 to 50° C., 20 to 80° C., 20 to 70° C., 20 to 60° C., 20 to 50° C., 30 to 80° C., 30 to 70° C., 30 to 60° C., 30 to 50° C., 40 to 80° C., 40 to 70° C., 40 to 60° C., or 40 to 50° C.) may have (1) a decursin content of about 2000 mg or more, about 2200 mg or more, about 2400 mg or more, about 2600 mg or more, or about 2800 mg or more, about 3000 mg or more, for example, 2000 to 5000 mg, 2000 to 4500 mg, 2000 to 4000 mg, 2000 to 3500 mg, 2200 to 5000 mg, 2200 to 4500 mg, 2200 to 4000 mg, 2200 to 3500 mg, 2400 to 5000 mg, 2400 to 4500 mg, 2400 to 4000 mg, 2400 to 3500 mg, 2600 to 5000 mg, 2600 to 4500 mg, 2600 to 4000 mg, 2600 to 3500 mg, 2800 to 5000 mg, 2800 to 4500 mg, 2800 to 4000 mg, 2800 to 3500 mg, 3000 to 5000 mg, 3000 to 4500 mg, 3000 to 4000 mg, or 3000 to 3500 mg, and/or (2) a decursinol angelate content of about 1200 mg or more, about 1400 mg or more, about 1600 mg or more, or about 1800 mg or more, for example, 1200 to 3000 mg, 1200 to 2800 mg, 1200 to 2600 mg, 1200 to 2400 mg, 1200 to 2200 mg, 1400 to 3000 mg, 1400 to 2800 mg, 1400 to 2600 mg, 1400 to 2400 mg, 1400 to 2200 mg, 1600 to 3000 mg, 1600 to 2800 mg, 1600 to 2600 mg, 1600 to 2400 mg, 1600 to 2200 mg, 1800 to 3000 mg, 1800 to 2800 mg, 1800 to 2600 mg, 1800 to 2400 mg, or 1800 to 2200 mg, and/or (3) a nodakenin content of about 800 mg or more, about 1000 mg or more, about 1200 mg or more, about 1500 mg or more, about 1700 mg or more, about 2000 mg or more, about 2200 mg or more, about 2500 mg or more, or about 2700 or more, for example, 800 to 5000 mg, 800 to 4500 mg, 800 to 4000 mg, 800 to 3500 mg, 800 to 3200 mg, 1000 to 5000 mg, 1000 to 4500 mg, 1000 to 4000 mg, 1000 to 3500 mg, 1000 to 3200 mg, 1200 to 5000 mg, 1200 to 4500 mg, 1200 to 4000 mg, 1200 to 3500 mg, 1200 to 3200 mg, 1500 to 5000 mg, 1500 to 4500 mg, 1500 to 4000 mg, 1500 to 3500 mg, 1500 to 3200 mg, 1700 to 5000 mg, 1700 to 4500 mg, 1700 to 4000 mg, 1700 to 3500 mg, 1700 to 3200 mg, 2000 to 5000 mg, 2000 to 4500 mg, 2000 to 4000 mg, 2000 to 3500 mg, 2000 to 3200 mg, 2200 to 5000 mg, 2200 to 4500 mg, 2200 to 4000 mg, 2200 to 3500 mg, 2200 to 3200 mg, 2500 to 5000 mg, 2500 to 4500 mg, 2500 to 4000 mg, 2500 to 3500 mg, 2500 to 3200 mg, 2700 to 5000 mg, 2700 to 4500 mg, 2700 to 4000 mg, 2700 to 3500 mg, or 2700 to 3200 mg, and/or (4) a beta-sitosterol content of 30 mg or more, 50 mg or more, 100 mg or more, 150 mg or more, 200 mg or more, 250 mg or more, or 300 mg or more, for example, 30 to 1000 mg, 30 to 800 mg, 30 to 600 mg, 30 to 500 mg, 30 to 400 mg, 50 to 1000 mg, 50 to 800 mg, 50 to 600 mg, 50 to 500 mg, 50 to 400 mg, 100 to 1000 mg, 100 to 800 mg, 100 to 600 mg, 100 to 500 mg, 100 to 400 mg, 150 to 1000 mg, 150 to 800 mg, 150 to 600 mg, 150 to 500 mg, 150 to 400 mg, 200 to 1000 mg, 200 to 800 mg, 200 to 600 mg, 200 to 500 mg, 200 to 400 mg, 250 to 1000 mg, 250 to 800 mg, 250 to 600 mg, 250 to 500 mg, 250 to 400 mg, 300 to 1000 mg, 300 to 800 mg, 300 to 600 mg, 300 to 500 mg, or 300 to 400 mg, based on total 100 g of the extract.

The mixed extract of *Angelica gigas* Nakai and *Cnidium officinale* may be a mixture of *Angelica gigas* Nakai extract and *Cnidium officinale* extract or an extract of a mixture of *Angelica gigas* Nakai and *Cnidium officinale*.

The extract of *Angelica gigas* Nakai is the same as described above.

The extract of *Cnidium officinale* may be obtained by extracting *Cnidium officinale* (whole body or root) with one or more extraction solvents selected from the group consisting of water and linear or branched alcohol having 1 to 4 carbon atoms. For example, the extract of *Cnidium officinale* may be an extract of 90 to 100% (v/v), 92 to 100% (v/v), 96 to 100% (v/v), or 98 to 100% (v/v) ethanol aqueous solution (e.g., 98% (v/v) ethanol aqueous solution) of *Cnidium officinale* (e.g., root). Further, the extract of *Cnidium officinale* may be extracted at 10 to 80° C., 10 to 70° C., 10 to 60° C., 10 to 50° C., 20 to 80° C., 20 to 70°

C., 20 to 60° C., 20 to 50° C., 30 to 80° C., 30 to 70° C., 30 to 60° C., 30 to 50° C., 40 to 80° C., 40 to 70° C., 40 to 60° C., or 40 to 50° C.

The extract of the mixture of *Angelica gigas* Nakai and *Cnidium officinale* may be obtained by extracting the mixture of *Angelica gigas* Nakai (root) and *Cnidium officinale* (whole body or root) with one or more extraction solvents selected from the group consisting of water and linear or branched alcohol having 1 to 4 carbon atoms. For example, the mixed extract may be (1) an extract of 90 to 100% (v/v), 92 to 100% (v/v), 96 to 100% (v/v), or 98 to 100% (v/v) ethanol aqueous solution (e.g., 98% (v/v) ethanol aqueous solution) of the mixture of *Angelica gigas* Nakai (root) and *Cnidium officinale* (e.g., root), or (2) a mixture of the extract of 90 to 100% (v/v), 92 to 100% (v/v), 96 to 100% (v/v), or 98 to 100% (v/v) ethanol aqueous solution (e.g., 98% (v/v) ethanol aqueous solution) of *Angelica gigas* Nakai (root) and the extract of 90 to 100% (v/v), 92 to 100% (v/v), 96 to 100% (v/v), or 98 to 100% (v/v) ethanol aqueous solution (e.g., 98% (v/v) ethanol aqueous solution) of *Cnidium officinale* (e.g., root). Further, the mixed extract may be extracted at 10 to 80° C., 10 to 70° C., 10 to 60° C., 10 to 50° C., 20 to 80° C., 20 to 70° C., 20 to 60° C., 20 to 50° C., 30 to 80° C., 30 to 70° C., 30 to 60° C., 30 to 50° C., 40 to 80° C., 40 to 70° C., 40 to 60° C., or 40 to 50° C.

A mixing ratio of the *Angelica gigas* Nakai extract and the *Cnidium officinale* extract in the mixture of the *Angelica gigas* Nakai extract and the *Cnidium officinale* extract or a mixing ratio of *Angelica gigas* Nakai and *Cnidium officinale* in the mixture of *Angelica gigas* Nakai and *Cnidium officinale* may be 1:1 to 5:1, 1.5:1 to 5:1, 1.5:1 to 4:1, 1.5:1 to 3:1, 1.5:1 to 2:1, 2:1 to 5:1, 2:1 to 4:1, 2:1 to 3:1, or 3:1 to 4:1 (a weight of *Angelica gigas* Nakai or a solid weight of *Angelica gigas* Nakai extract:a weight of *Cnidium officinale* or a solid weight of *Cnidium officinale* extract). The solid weight means a weight of *Angelica gigas* Nakai or *Cnidium officinale*, or the solid weight means a weight of a solid remaining after removing the solvent from the extract when the mixture is a mixture of extracts. The solid weight is a term used to denote that the mixing ratio means a weight ratio between the active ingredients excluding the extraction solvents so as not to be influenced by the properties and/or concentrations of the extracts when the mixture is a mixture of the *Angelica gigas* Nakai extract and the *Cnidium officinale* extract.

The extract of *Angelica gigas* Nakai or the mixed extract of *Angelica gigas* Nakai and *Cnidium officinale* which is comprised as the active ingredient in the pharmaceutical composition may be in a form of a dry product, a concentrate, or a concentrated dry product.

A content of the extract of *Angelica gigas* Nakai or the mixed extract of *Angelica gigas* Nakai and *Cnidium officinale* which is comprised as the active ingredient in the pharmaceutical composition may be appropriately controlled by type and purpose of use, the patient's condition, the type and severity of symptoms. The content may be 0.001% by weight to 99.9% by weight, 0.01% by weight to 70% by weight, or 0.1% by weight to 50% by weight, based on the solid weight, but is not limited thereto. The solid weight means the weight of the solid remaining after removing the solvent from the extract, as described above.

A subject to be administered with a pharmaceutically effective amount of the pharmaceutical composition or the active ingredient may be mammals comprising humans, dogs, cats, horses, cattle, pigs, goats, rabbits, mice, rats, etc., or cells or tissues separated therefrom or cultures thereof. They may be administered via a variety of routes. The administration may be performed via any route commonly used, for example, oral administration or parenteral administration such as intravenous administration, intramuscular administration, subcutaneous administration, intraperitoneal administration, and topical administration of a site of lesion (e.g., joint). The pharmaceutical composition may be formulated into oral preparations such as a powder, a granule, a tablet, a capsule, a suspension, an emulsion, a syrup, an aerosol, etc., or parenteral preparations such as a transdermal preparation, a suppository, and a sterile injectable solution, according to the common methods.

The pharmaceutical composition may further comprise a pharmaceutically suitable and physiologically acceptable additive such as a carrier, an excipient, and/or a diluent, in addition to the extract of *Angelica gigas* Nakai. Examples of the carrier, excipient, or diluent may comprise one or more selected from the group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oils. Such preparations may be formulated using one or more diluents or excipients selected from the group consisting of a filler, an extender, a binder, a wetting agent, a disintegrating agent, and a surfactant ordinarily employed. Examples of the solid preparation for oral administration comprise one or more selected from the group consisting of a tablet, a pill, a powder, a granule, a capsule, a syrup, a powder, a suspension, etc., and the solid preparation may be prepared by mixing the extract with one or more excipients, for example, selected from the group consisting of starch, calcium carbonate, sucrose, lactose, and gelatin. Further, in addition to the simple excipients, lubricants such as magnesium stearate and talc may be used. Examples of a liquid preparation for oral administration may comprise one or more selected from the group consisting of a suspension, a liquid for internal use, an emulsion, and a syrup. Various excipients, for example, one or more selected from the group consisting of a wetting agent, a sweetener, a flavor, and a preservative may be comprised, in addition to commonly used simple diluents such as water and liquid paraffin. The preparation for parenteral administration may comprise one or more selected from the group consisting of a sterilized aqueous solution, a non-aqueous solvent, a suspension, an emulsion, a lyophilized formulation, a suppository, a transdermal preparation, etc. As the non-aqueous solvent or the suspension, one or more selected from the group consisting of propylene glycol, polyethylene glycol, vegetable oil such as olive oil, injectable ester such as ethyl oleate, etc. may be used.

The pharmaceutical composition may be administered in a pharmaceutically effective amount. An administration dose of the pharmaceutical composition may vary depending on factors such as a formulation method, administration mode, a patient's age, body weight, gender, health state, and diet, administration time, administration frequency, administration routes, excretion rates, and responsiveness. The administration dose may vary depending on a patient's age, body weight, gender, administration mode, health condition, and disease severity, and the pharmaceutical composition may be administered in a single dose or divided into several doses per day at a predetermined time interval according to the instructions of a physician or a pharmacist. For example, a daily dose of the pharmaceutical composition may be 0.001 mg/kg to 1000 mg/kg, specifically 0.01 mg/kg to 100 mg/kg, and more specifically 0.1 mg/kg to 20 mg/kg, based on a solid weight of the active ingredient (the extract of *Angelica gigas* Nakai or the mixed extract of *Angelica gigas* Nakai and *Cnidium officinale*), but is not limited thereto. The daily dose may be prepared as a single formulation in a unit dosage form, or prepared in an appropriate divided dosage form, or prepared in multi-unit dosage forms. The above-mentioned doses are exemplary of the average case, and the doses may be higher or lower depending on individual differences.

Another embodiment provides a method of preparing a composition having effects of preventing, treating, and/or improving osteoarthritis, comprising a step of preparing the extract of *Angelica gigas* Nakai. The step of preparing the extract of *Angelica gigas* Nakai may comprise the step of extracting the root of *Angelica gigas* Nakai at 10° C. to 80° C., 10° C. to 70° C., 10° C. to 60° C., 10° C. to 50° C., 20° C. to 80° C., 20° C. to 70° C., 20° C. to 60° C., 20° C. to 50° C., 30° C. to 80° C., 30° C. to 70° C., 30° C. to 60° C., 30° C. to 50° C., 40° C. to 80° C., 40° C. to 70° C., 40° C. to 60° C., or 40° C. to 50° C. with one or more selected from the group consisting of water and linear or branched alcohol having 1-4 carbon atoms (e.g., ethanol), for example, 90 to 100% (v/v), 92 to 100% (v/v), 96 to 100% (v/v), or 98 to 100% (v/v) ethanol aqueous solution (e.g., 98% (v/v) ethanol aqueous solution) of 1 to 10 volume times, 2 to 8 volume times, or 4 to 6 volume times. The extraction may be performed for any time, as long as the extraction sufficiently occurs, and the extraction time may be determined as 1 hr or longer, 2 hrs or longer, 3 hrs or longer, or 4 hrs or longer, for example, 1 hr to 12 hrs, 2 hrs to 12 hrs, 3 hrs to 12 hrs, 4 hrs to 12 hrs, 1 hr to 6 hrs, 2 hrs to 6 hrs, 3 hrs to 6 hrs, or 4 hrs to 6 hrs, but is not limited thereto.

Still another aspect provides a method of preparing a composition having effects of preventing, treating, and/or improving osteoarthritis, comprising the step of preparing the mixed extract of *Angelica gigas* Nakai and *Cnidium officinale*.

The step of preparing the mixed extract of *Angelica gigas* Nakai and *Cnidium officinale* may comprise the step of 1) mixing the *Angelica gigas* Nakai extract and the *Cnidium officinale* extract, or 2) extracting a mixture of *Angelica gigas* Nakai and *Cnidium officinale* with an extraction solvent. The extraction solvent and extraction temperature used in the extraction step may be determined by referring to the above description regarding the extract of *Angelica gigas* Nakai.

For example, the step of 1) mixing the *Angelica gigas* Nakai extract and the *Cnidium officinale* extract may comprise the steps of i) extracting the root of *Angelica gigas* Nakai at 10° C. to 80° C., 10° C. to 70° C., 10° C. to 60° C., 10° C. to 50° C., 20° C. to 80° C., 20° C. to 70° C., 20° C. to 60° C., 20° C. to 50° C., 30° C. to 80° C., 30° C. to 70° C., 30° C. to 60° C., 30° C. to 50° C., 40° C. to 80° C., 40° C. to 70° C., 40° C. to 60° C., or 40° C. to 50° C. with one or more selected from the group consisting of water and linear or branched alcohol having 1-4 carbon atoms (e.g., ethanol), for example, 90 to 100% (v/v), 92 to 100% (v/v), 96 to 100% (v/v), or 98 to 100% (v/v) ethanol aqueous solution (e.g., 98% (v/v) ethanol aqueous solution) of 1 to 10 volume times, 2 to 8 volume times, or 4 to 6 volume times, ii) extracting the root of *Cnidium officinale* at 10° C. to 80° C., 10° C. to 70° C., 10° C. to 60° C., 10° C. to 50° C., 20° C. to 80° C., 20° C. to 70° C., 20° C. to 60° C., 20° C. to 50° C., 30° C. to 80° C., 30° C. to 70° C., 30° C. to 60° C., 30° C. to 50° C., 40° C. to 80° C., 40° C. to 70° C., 40° C. to 60° C., or 40° C. to 50° C. with one or more selected from the group consisting of water and linear or branched alcohol having 1-4 carbon atoms (e.g., ethanol), for example, 90 to 100% (v/v), 92 to 100% (v/v), 96 to 100% (v/v), or 98 to 100% (v/v) ethanol aqueous solution (e.g., 98% (v/v) ethanol aqueous solution) of 1 to 10 volume times, 2 to 8 volume times, or 4 to 6 volume times, and iii) mixing the extract of *Angelica gigas* Nakai extracted in step i) and the extract of *Cnidium officinale* extracted in step ii).

The step of 2) extracting a mixture of *Angelica gigas* Nakai and *Cnidium officinale* with an extraction solvent may comprise the steps of i') preparing a mixture by mixing the *Angelica gigas* Nakai root and the *Cnidium officinale* root, and ii') extracting the mixture at 10° C. to 80° C., 10° C. to 70° C., 10° C. to 60° C., 10° C. to 50° C., 20° C. to 80° C., 20° C. to 70° C., 20° C. to 60° C., 20° C. to 50° C., 30° C. to 80° C., 30° C. to 70° C., 30° C. to 60° C., 30° C. to 50° C., 40° C. to 80° C., 40° C. to 70° C., 40° C. to 60° C., or 40° C. to 50° C. with one or more selected from the group consisting of water and linear or branched alcohol having 1-4 carbon atoms (e.g., ethanol), for example, 90 to 100% (v/v), 92 to 100% (v/v), 96 to 100% (v/v), or 98 to 100% (v/v) ethanol aqueous solution (e.g., 98% (v/v) ethanol aqueous solution) of 1 to 10 volume times, 2 to 8 volume times, or 4 to 6 volume times.

In the extraction step, the extraction may be performed for any time, as long as the extraction sufficiently occurs, and the extraction time may be determined as 1 hr or longer, 2 hrs or longer, 3 hrs or longer, or 4 hrs or longer, for example, 1 hr to 24 hrs, 2 hrs to 24 hrs, 3 hrs to 24 hrs, 4 hrs to 24 hrs, 1 hr to 12 hrs, 2 hrs to 12 hrs, 3 hrs to 12 hrs, 4 hrs to 12 hrs, 1 hr to 6 hrs, 2 hrs to 6 hrs, 3 hrs to 6 hrs, or 4 hrs to 6 hrs, but is not limited thereto.

A mixing ratio of the extract of *Angelica gigas* Nakai and the extract of *Cnidium officinale* or a mixing ratio of *Angelica gigas* Nakai and *Cnidium officinale* is the same as described above.

The extraction procedures used in the method may be performed by any extraction method commonly used, and for example, by one or more methods selected from the group consisting of hot water extraction, ultrasonic extraction, and reflux extraction, but are not limited thereto.

Still another embodiment provides a health functional food for preventing and/or improving osteoarthritis, comprising the extract of *Angelica gigas* Nakai. Still another aspect provides a health functional food for preventing and/or improving osteoarthritis, comprising the mixed extract of *Angelica gigas* Nakai and *Cnidium officinale*.

The health functional food may be a food prepared by using raw materials or ingredients (hereinafter, referred to as 'functional raw materials') having nutrients which may be deficient in the daily diet or having functions useful for the human body, and the health functional food means all foods that help to maintain health or to prevent and/or improve a certain disease or symptom, and a type of the final product is not particularly limited. For example, the health functional food may be selected from the group consisting of a variety of foods, beverage compositions, food additives, etc., but is not limited thereto.

A content of the extract of *Angelica gigas* Nakai or the mixed extract of *Angelica gigas* Nakai and *Cnidium officinale* in the health functional food is appropriately controlled according to the type of the food, desired use, etc., but it not particularly limited. For example, the content may be 0.001% by weight to 95% by weight or 0.01% by weight to 90% by weight, based on the total weight of the food.

The health functional food may further comprise one or more selected from the group consisting of a variety of nutrients, vitamins, minerals (electrolytes), a flavoring agent such as a synthetic or natural flavoring agent, a colorant, a filler (cheese, chocolate, etc.), pectic acid and salts thereof, alginic acid and salts thereof, organic acids, a protective colloidal thickener, a pH modifier, a stabilizer, a preservative, glycerin, alcohol, a carbonating agent used in carbonated beverages, etc. In addition, the health functional food, in particular, the health functional beverage compositions may comprise pulp for the preparation of a natural fruit juice, a fruit juice drink, or a vegetable drink. Such ingredients may be used singly or in any combination thereof. The proportion of the additives is generally selected in the range of about 0.001 parts by weight to about 20 parts by weight, based on 100 parts by weight of the total health functional food, but is not limited thereto.

The extract of *Angelica gigas* Nakai suppresses production of inflammatory mediators in osteoarthritis-induced knee articular cartilage tissues and inhibits destruction of proteoglycan (PG) and glycosaminoglycan (GAG), thereby exhibiting excellent therapeutic effects on osteoarthritis.

EXAMPLES

Hereafter, the present invention will be described in detail by examples. The following examples are intended merely to illustrate the invention and are not construed to restrict the invention.

Example 1: Preparation of Extract 1.1. Preparation of Extract of *Angelica gigas* Nakai The roots of *Angelica gigas* Nakai were washed with clean water, and then sufficiently dried. The dried roots of *Angelica gigas* Nakai were pulverized to obtain powder. To 100 g of the obtained powder, 5 volume times (500 ml) of ethanol (98% (v/v) ethanol) was added and extracted at 40° C.~50° C. for 4 hours or longer. A filtrate filtered through a 1 μm (micrometer) filter was concentrated by heating to 10% of its original weight. While crystalline cellulose was slowly added to the obtained concentrate, the concentrate was further concentrated, completely dried, and then pulverized to prepare a powder of *Angelica gigas* Nakai ethanol extract.

1.2. Preparation of Extract of *Cnidium officinale*

The roots of *Cnidium officinale* were washed with clean water, and then sufficiently dried. The dried roots were pulverized to obtain powder. To 100 g of the obtained powder, 5 volume times (500 ml) of ethanol (98% (v/v) ethanol) was added and extracted at 40° C.~50° C. for 4 hours or longer. A filtrate filtered through a 1 μm (micrometer) filter was concentrated by heating to 10% of its original weight. While crystalline cellulose was slowly added to the obtained concentrate, the concentrate was further concentrated, completely dried, and then pulverized to prepare a powder of *Cnidium officinale* ethanol extract.

1.3. Preparation of Mixed Extract of *Angelica gigas* Nakai and *Cnidium officinale* (1:1, 2:1, 4:1 and 5:1 Mixed Extract)

The powder of *Angelica gigas* Nakai ethanol extract prepared in Example 1.1 and the powder of *Cnidium officinale* ethanol extract prepared in Example 1.2 were mixed at a weight ratio of 1:1, 2:1, 4:1, and 5:1 (the weight of *Angelica gigas* Nakai:the weight of *Cnidium officinale*) to prepare 1:1, 2:1, 4:1, and 5:1 mixed extracts of *Angelica gigas* Nakai and *Cnidium officinale*.

Comparative Example 1: Preparation of Water Extract of *Angelica gigas* Nakai 5,000 ml of distilled water was added to 2 kg of *Angelica gigas* Nakai, and extracted in water bath (about 90° C.) for 8 hours four times, and then filtered. The solvent was evaporated by using a concentrator to obtain an herbal medicine extract. The obtained extract was freeze-dried in a freeze-dryer for 12 hours, and pulverized to prepare a powder of *Angelica gigas* Nakai water extract in the form of a dry powder.

Comparative Example 2: Preparation of Mixed Water Extract of *Angelica gigas* Nakai and *Cnidium officinale* (1:1, 2:1, 4:1 and 5:1 Mixed Extract)

5,000 ml of distilled water was added to 2 kg of *Cnidium officinale*, and extracted in water bath for 8 hours four times, and then filtered. The solvent was evaporated by using a concentrator to obtain an herbal medicine extract. The obtained extract was freeze-dried in a freeze-dryer for 12 hours, and pulverized to prepare a powder of *Cnidium officinale* water extract in the form of a dry powder. The obtained powder of *Cnidium officinale* water extract and the powder of *Angelica gigas* Nakai water extract obtained in Comparative Example 1 were mixed at a weight ratio of 2:1 (the weight of *Angelica gigas* Nakai: the weight of *Cnidium officinale*) to prepare a mixed water extract of *Angelica gigas* Nakai and *Cnidium officinale*.

Comparative Example 3: Preparation of Cold Ethanol Extract of *Angelica gigas* Nakai 1 pack (168 g) of *Angelica gigas* Nakai was pulverized using a herbal medicine grinder in a size of 100-200 mesh, and then about 1,500 ml (about 1:10 weight/volume) of 95% (v/v) ethanol was added thereto, followed by cold immersion extraction for 5 days. Solids in the extract were removed using a Whatman filter paper NO. 4, and then concentrated under reduced pressure using a rotary vacuum evaporator to obtain a cold ethanol extract of *Angelica gigas* Nakai. The obtained extract was freeze-dried using a freeze-dryer for 12 hours and pulverized to prepare a cold ethanol extract of *Angelica gigas* Nakai in the form of a dry powder.

Comparative Example 4: Preparation of Mixed Cold Ethanol Extract of *Angelica gigas* Nakai and *Cnidium officinale*

1 pack (168 g) of *Cnidium officinale* was pulverized using a herbal medicine grinder in a size of 100-200 mesh, and then about 1,500 ml (about 1:10 weight/volume) of 95% (v/v) ethanol was added thereto, followed by cold immersion extraction for 5 days. Solids in the extract were removed using a Whatman filter paper NO. 4, and then concentrated under reduced pressure using a rotary vacuum evaporator to obtain a cold ethanol extract of *Cnidium officinale*. The obtained cold ethanol extract of *Cnidium officinale* and the cold ethanol extract of *Angelica gigas* Nakai obtained in Comparative Example 3 were mixed at a weight ratio of 2:1 (the weight of *Angelica gigas* Nakai: the weight of *Cnidium officinale*) to prepare a mixed cold ethanol extract of *Angelica gigas* Nakai and *Cnidium officinale*. The obtained mixed extract was freeze-dried using a freeze-dryer for 12 hours and pulverized to prepare a mixed cold ethanol extract of *Angelica gigas* Nakai and *Cnidium officinale* in the form of a dry powder.

Reference Example 1: Preparation of Experimental Animal 1

60 male 6-week-old Sprague-Dawley white rats (Orient bio, Korea) were purchased and acclimated at a temperature of 23±2° C. and humidity of 55±5% on a 12-hour light/dark cycle for 1 week, and used in experiments. During an experimental period, the rats were given free access to a feed for experimental animals (Samyang Oil & Feed Corporation, Korean) and sterile drinking water.

The body weights of the experimental animals that had been adapted for 1 week were measured and uniformly divided into 5 groups (a normal group, a control group, a treated group 1, a treated group 2, and a treated group 3), each including 12 rats. To induce osteoarthritis, white rats were anesthetized by administering with an anesthetic mixture of Zoletile (Bayer Korea (Korea)) and Rumpun (Bayer Korea (Korea)) at a weight ratio of 2:1. Then, both knees were shaved, and 0.1 mL of MIA (monosodium iodoacetate, 30 mg/mL; Sigma Chemical Co., USA) solution diluted with physiological saline was injected into both knee joint cavities by using a 1 mL syringe.

In the normal group (N), each 0.1 mL of injectable physiological saline was injected into both knee joint cavities, and 1 mL of distilled water was orally administered once daily for 2 days. In the control group (C), each 0.1 mL of MIA was injected into both knee joint cavities to induce osteoarthritis, and 1 mL of distilled water was orally administered once daily for 2 days. In the treated groups (25, 50 and 100 mg/kg), each 0.1 mL of MIA was injected into both knee joint cavities to induce osteoarthritis, and 1 mL of a test material, which was prepared by diluting the powder of *Angelica gigas* Nakai ethanol extract prepared in Example 1.1 or the powder of the mixed extract of *Angelica gigas* Nakai and *Cnidium officinale* prepared in Example 1.3 with distilled water at a concentration of 25 mg/kg, 50 mg/kg, and 100 mg/kg, respectively, was orally administered once daily for 2 days.

Reference Example 2: Preparation of Experimental Cells

A cartilage tissue was separated from the joint of 2~3-week-old New Zealand white rabbit, and cultured in a DMEM (Dulbecco's Modified Eagle's Medium, Gibco BRL) medium containing 10% fetal bovine serum (Gibco BRL, Grand Island, N.Y., USA) under conditions of 37° C. and 5% $CO_2$ to prepare rabbit chondrocytes.

Reference Example 3: Preparation of Experimental Animal 2

The body weights of the experimental animals that had been adapted for 1 week in an animal room as in Reference Example 1 were measured and uniformly divided into 3 groups (a normal group, a control group, and a treated group), each including 10 rats.

In the normal group, each 0.1 mL of injectable physiological saline was injected into both knee joint cavities, and 1 mL of distilled water was orally administered once daily for 3 weeks. In the control group, each 0.1 mL of MIA was injected into both knee joint cavities to induce osteoarthritis, and 1 mL of distilled water was orally administered once daily for 3 weeks. In the treated group, each 0.1 mL of MIA was injected into both knee joint cavities to induce osteoarthritis, and 1 mL of a test material, which was prepared by diluting the powder of *Angelica gigas* Nakai extract prepared in Example 1.1, the powder of the mixed extract of *Angelica gigas* Nakai and *Cnidium officinale* prepared in Example 1.3, or the water extract of *Angelica gigas* Nakai prepared in Comparative Example 1 with distilled water at a concentration of 100 mg/kg, respectively, was orally administered once daily for 3 weeks.

Reference Example 4: Statistical Treatment

The quantitative results obtained in the following Examples 2 to 6 were statistically analyzed by the unpaired student's t-test using SPSS 11.0. Significance was tested at the levels of $p<0.05$ and ** $p<0.01$, and the results were expressed as mean±standard deviation.

The quantitative results obtained in the following Examples 7 to 11 were analyzed by the student's t-test using SPSS (SPSS 10.1). Significance was tested at the $p<0.01$ level, and the results were expressed as mean±standard deviation.

Example 2: Cytotoxicity Test

In order to examine cytotoxicity of the extract of *Angelica gigas* Nakai, WST (water soluble tetrazolium salt) assay was performed using a cell counting kit-8 (Dojindo, Japan). The rabbit chondrocytes prepared in Reference Example 2 were seeded in a 96-well plate at a density of $1\times10^5$ cells/well and cultured for 12 hours. Next, the chondrocytes were treated with different concentrations (0, 5, 10, 25 and 50 μg/mL) of the powder of the ethanol extract of *Angelica gigas* Nakai prepared in Example 1.1 for 24 hours. 10 μl of WST-8 solution (Dojindo, Japan) per well was added and allowed to react under conditions of 37° C. and 5% $CO_2$ for 3 hours, and absorbance at 450 nm was measured using an ELISA reader (BIO-TEK Instruments Inc., Power wave X340, Winooski, Vt., USA) to obtain cell viability according to treatment of the extract of *Angelica gigas* Nakai. The experimental values were expressed as a percentage relative to a control group which was not treated with the powder of *Angelica gigas* Nakai extract.

The results are shown in FIG. 1. As shown in FIG. 1, cell viability of 100% or more was observed at all concentrations used in the experiments, indicating no cytotoxicity of the ethanol extract of *Angelica gigas* Nakai.

Example 3: Measurement of NO (Nitric Oxide) Production

In order to examine NO production inhibition of the extract of *Angelica gigas* Nakai, Griess reagent assay was used. The rabbit chondrocytes prepared in Reference Example 2 were seeded in a 96-well plate at a density of $1\times10^5$ cells/well, and cultured for 12 hours. The chondrocytes were treated with IL-1α (interleukin-1α, Miltenyi Biotec., Germany) and the powder of the ethanol extract of *Angelica gigas* Nakai prepared in Example 1.1 (treatment concentrations: 0, 5, 10, 25 and 50 μg/mL) singly or in combination, followed by incubation for 24 hours. IL-1α was used to induce inflammation, and used in an amount of 5 μg (microgram)/ml. An equal amount of Griess reagent (1% sulfanilamide and 0.1% N-[1-naphthy]-ethylenediamine dihydrochloride in 5% phosphoric acid) was added to the culture medium, and allowed to react at room temperature for 10 minutes. Then, absorbance at 540 nm was measured using an ELISA reader. NO concentrations were determined from a calibration curve obtained by using $NaNO_2$ standard solutions.

Figure 2:
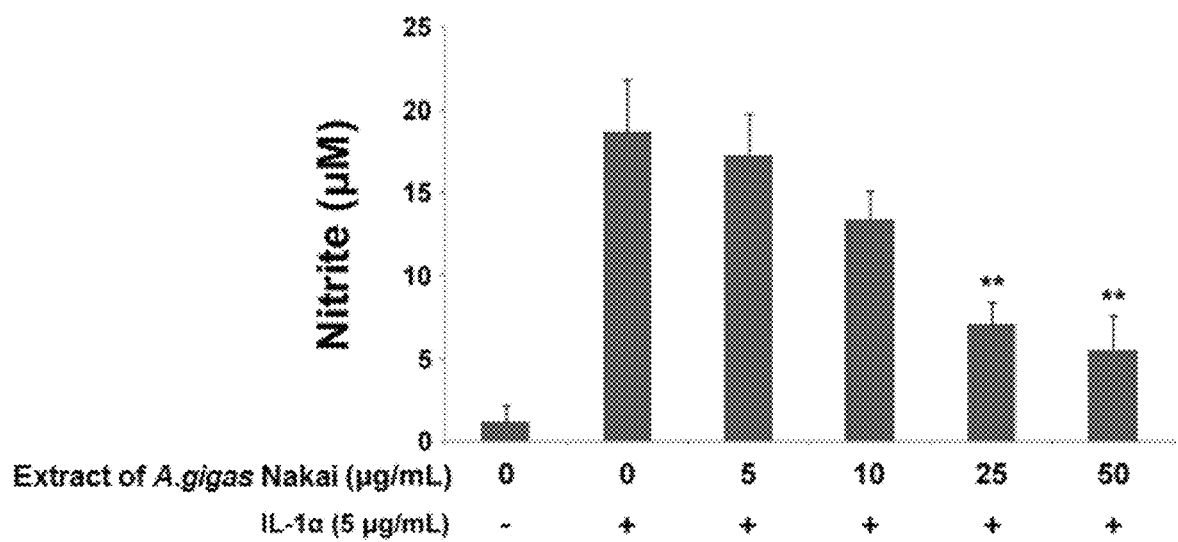
FIG. 2 is a graph showing NO production according to concentrations of the *Angelica gigas* Nakai extract, after rabbit chondrocytes with IL-1α-induced inflammation were treated with the *Angelica gigas* Nakai extract, and then cultured for 24 hours.

The results are shown in FIG. 2. As shown in FIG. 2, NO production in the rabbit chondrocytes treated with only IL-1α was about 20 μM (micromole), which was about 10 times increase in NO production, compared with the group treated with no IL-1α. When the ethanol extract of *Angelica gigas* Nakai with different concentrations was treated thereto, a reduction in NO production was observed in all test concentrations, indicating that the ethanol extract of *Angelica gigas* Nakai inhibits NO production under inflammation-induced environment.

Further, in order to examine the synergistic inhibitory effect of the mixed extract of *Angelica gigas* Nakai and *Cnidium officinale* on NO production, the ethanol extract of *Angelica gigas* Nakai prepared in Example 1.1 and the mixed extract of *Angelica gigas* Nakai and *Cnidium officinale* prepared in Example 1.3 were subjected to the same experiment as above. In this regard, treatment concentrations of the ethanol extract of *Angelica gigas* Nakai and the mixed extract of *Angelica gigas* Nakai and *Cnidium officinale* were 50 µg/mL, respectively.

Figure 16:
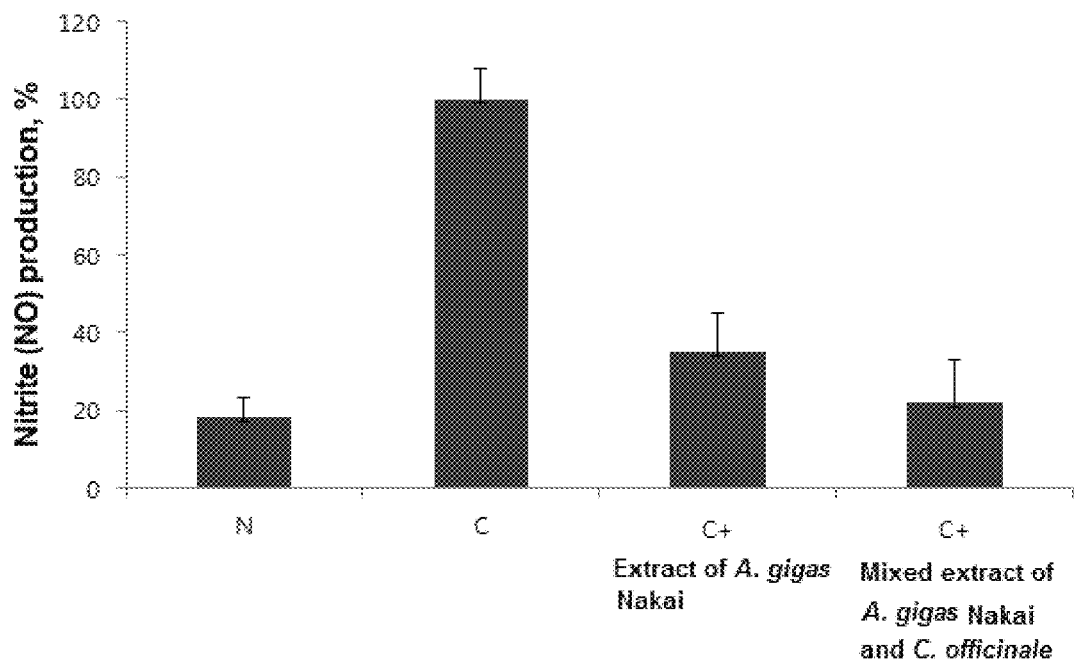
FIG. 16 is a graph showing NO production in rabbit chondrocytes with IL-1α-induced inflammation after treatment of the extract of *Angelica gigas* Nakai or the mixed extract of *Angelica gigas* Nakai and *Cnidium officinale*.

The obtained results are shown in FIG. 16. In FIG. 16, 'N' represents normal rabbit chondrocytes, 'C' represents rabbit chondrocytes treated with only IL-1α, 'C+*Angelica gigas* Nakai extract powder' represents rabbit chondrocytes treated with IL-1α and the ethanol extract of *Angelica gigas* Nakai, and 'C+*Angelica gigas* Nakai, *Cnidium officinale* mixed extract' represents rabbit chondrocytes treated with IL-1α and the mixed extract of *Angelica gigas* Nakai and *Cnidium officinale*. Each value was expressed as a relative value (%), when the NO production in 'rabbit chondrocytes treated with only IL-1α' was taken as 100%. As shown in FIG. 16, the rabbit chondrocytes treated with the ethanol extract of *Angelica gigas* Nakai or the mixed extract of *Angelica gigas* Nakai and *Cnidium officinale* showed a remarkable reduction in the NO production, compared with the rabbit chondrocytes treated with only IL-1α. In particular, a high reduction in NO production was observed in the rabbit chondrocytes treated with the mixed extract of *Angelica gigas* Nakai and *Cnidium officinale*.

Example 4: Measurement of Gene and Protein Levels of iNOS, COX-2, TNF-α, and IL-6 in Cartilage Tissues The inhibitory effects of *Angelica gigas* Nakai extract on gene and protein expressions of iNOS (inducible nitric oxide synthase), COX-2 (cyclooxygenase-2), TNF-α (tumor necrosis factor-α), IL-1β (interleukin-1β, and IL-6 (interleukin-6) were tested.

First, in order to examine the effects of *Angelica gigas* Nakai extract on expressions of iNOS (inducible nitric oxide synthase), COX-2 (cyclooxygenase-2), TNF-α (tumor necrosis factor-α), IL-1β (interleukin-1β, and IL-6 (interleukin-6) genes, RT-PCR was performed. MIA was injected into the experimental animals prepared in Reference Example 1 (the group administered with the ethanol extract powder of *Angelica gigas* Nakai), and after 2 days, the cartilages were separated and ground. From the cartilage tissues, total RNAs were separated using a total RNA extraction kit (iNtRON Biotechnology Inc., Korea). Total RNAs were quantified, and each cDNA was synthesized from an equal amount (1 µg) of the total RNA using an RT-PreMix (iNtRON Biotechnology Inc.). Respective primers corresponding to iNOS, COX-2, TNF-α, IL-1β, IL-6, and β-actin genes were used to perform RT-PCR under conditions of total 30 cycles of 94° C. 1 min, 50~65° C. 45 sec, and 72° C. 1 min. The primers used in RT-PCR are summarized in the following Table 1.

TABLE 1

| Gene | Primer sequence | Product length (bp) |
|------|-----------------|---------------------|
| iNOS | Forward: TTCTTTGCTTCTGTGCTTAATGCG (SEQ ID NO: 1)<br>Reverse: GTTGTTGCTGAACTTCCAATCGT (SEQ ID NO: 2) | 1061 |
| COX-2 | Forward: CTGCATGTGGCTGATGTCATC (SEQ ID NO: 3)<br>Reverse: AGGACCCGTCATCTCCAGGGTAATC (SEQ ID NO: 4) | 1061 |
| TNF-α | Forward: GTAGCCCACGTCGTAGCAAA (SEQ ID NO: 5)<br>Reverse: CCCTTCTCCAGCTGGAAGAC (SEQ ID NO: 6) | 346 |
| IL-1β | Forward TGATGTTCCCATTAGACAGC (SEQ ID NO: 7)<br>Reverse GAGGTGCTGATGTACCAGTT (SEQ ID NO: 8) | 378 |
| IL-10 | Forward: CAGTCAGCCAGACCCACAT (SEQ ID NO: 9)<br>Reverse: GCTCCACTGCCTTGCTTT (SEQ ID NO: 10) | 322 |
| β-actin | Forward: TTGTAACCAACTGGGACGATATGG (SEQ ID NO: 11)<br>Reverse: GATCTTGATCTTCATGGTGCTAG (SEQ ID NO: 12) | 764 |

Further, in order to examine the effects of *Angelica gigas* Nakai extract on iNOS and COX-2 protein productions, Western blot analysis was performed. MIA was injected into the experimental animals prepared in Reference Example 1 (the group administered with the ethanol extract powder of *Angelica gigas* Nakai), and after 2 days, the cartilages were separated and ground. Proteins in the cartilage tissues were collected using a lysis buffer (Cell Signaling, Danvers, Mass., USA). Protein concentrations were measured using a BCA protein assay reagent kit (Pierce, Rockford, Ill., USA), and then an equal amount (20 µg) of each protein was electrophoresed on a 10% SDS-PAGE gel, and transferred onto a nitrocellulose membrane (Whatman, Dassel, Germany). To block non-specific binding of antibodies, 5 wt % skim milk was added to the membrane, and allowed to react for 1 hour, and then replaced by 5 wt % skim milk containing anti-iNOS antibody (BD, USA), anti-COX-2 antibody (Santa Cruz Biotechnology Inc, Calif., USA), and anti-β-actin antibody (Sigma), and allowed to react 4° C. for 12 hours. The membrane was washed with TBST (50 mM Tris-HCl (pH 7.5), 150 mM NaCl, 0.1% Tween-20) for 5 minutes three times, and reacted with secondary antibody against each antibody at room temperature for 1 hour. Then, expression of each protein was examined using an ECL solution (Amersham Pharmacia Biotech., N.J., USA).

Figure 3:
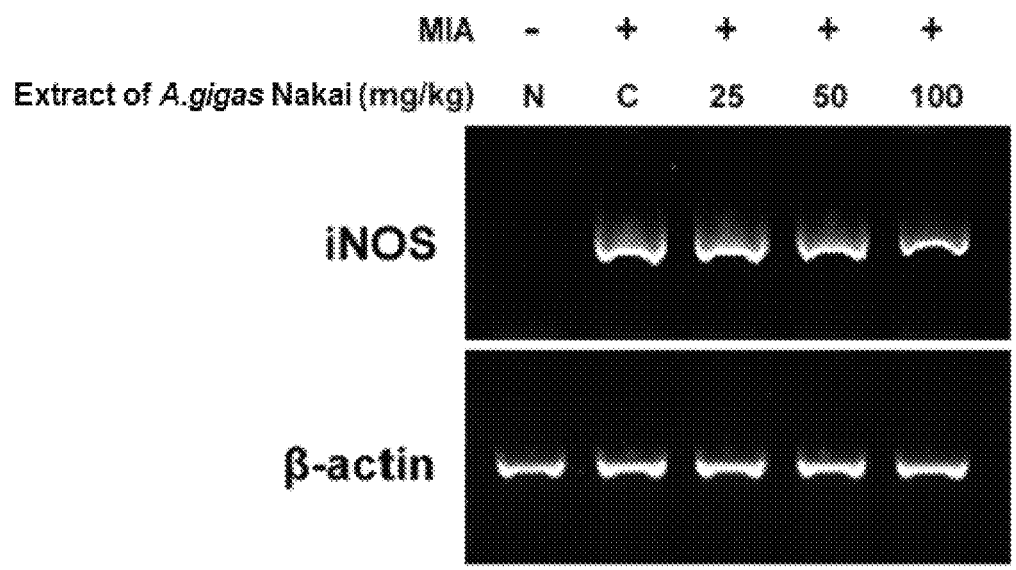
FIG. 3 is RT-PCR results showing changes in iNOS gene (mRNA) levels in cartilage tissues according to concentrations of the *Angelica gigas* Nakai extract, after treatment of the *Angelica gigas* Nakai extract.
Figure 4:
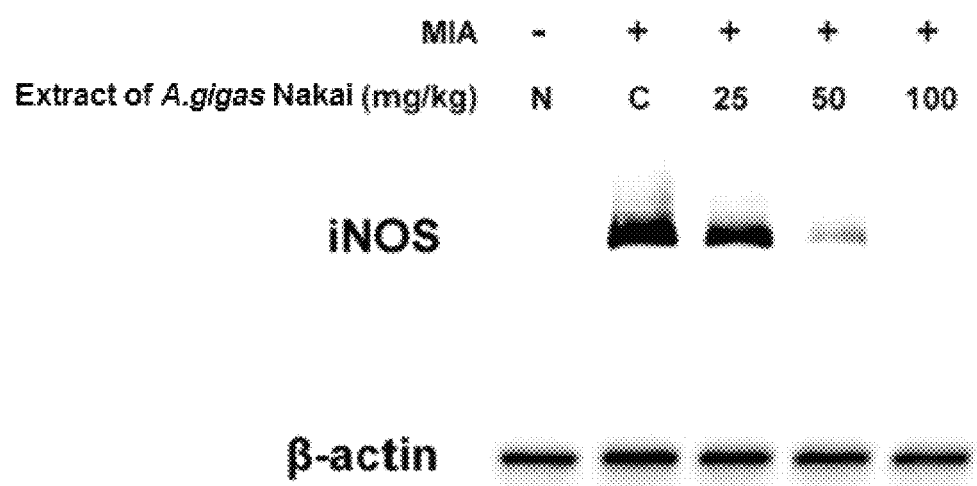
FIG. 4 is Western blotting results showing changes in iNOS protein levels in cartilage tissues according to concentrations of the *Angelica gigas* Nakai extract, after treatment of the *Angelica gigas* Nakai extract.

Changes in iNOS gene (mRNA) and protein expression levels according to treatment of the ethanol extract of *Angelica gigas* Nakai are shown in FIG. 3 (mRNA expression level) and FIG. 4 (protein expression level), respectively. As shown in FIGS. 3 and 4, both iNOS mRNA and protein expression levels were greatly increased in the control group (C), whereas both iNOS mRNA and protein expression levels were decreased in an *Angelica gigas* Nakai ethanol extract concentration-dependent manner in the treated groups (25, 50 and 100 mg/kg).

Figure 5:
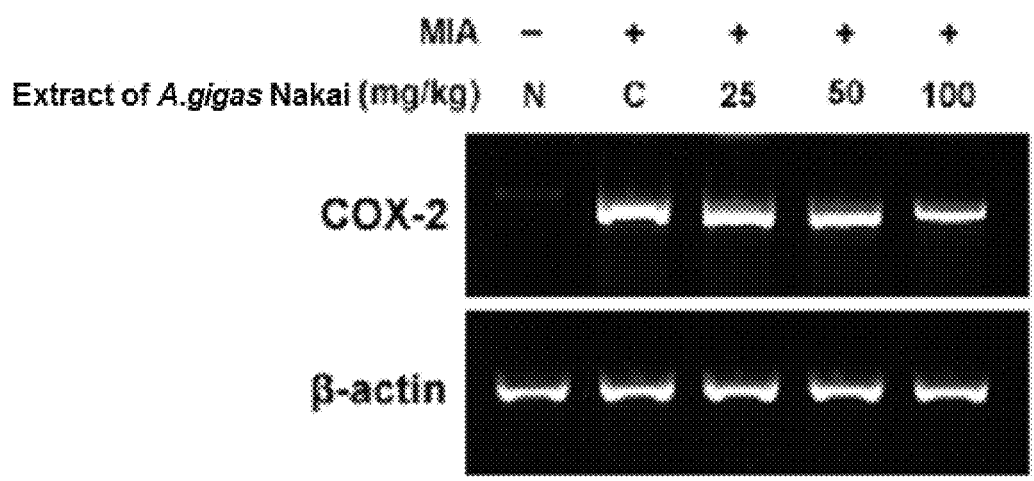
FIG. 5 is RT-PCR results showing changes in COX-2 gene (mRNA) levels in cartilage tissues according to concentrations of the *Angelica gigas* Nakai extract, after treatment of the *Angelica gigas* Nakai extract.
Figure 6:
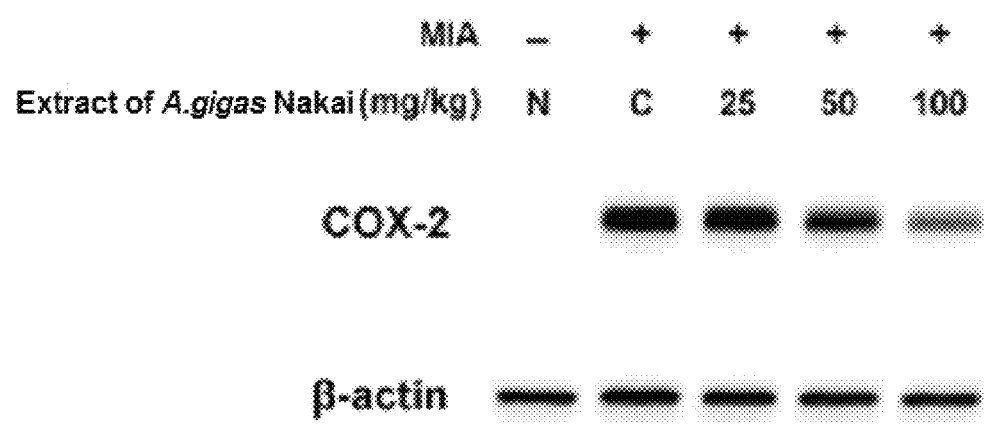
FIG. 6 is Western blotting results showing changes in COX-2 protein levels in cartilage tissues according to concentrations of the *Angelica gigas* Nakai extract, after treatment of the *Angelica gigas* Nakai extract.

Changes in COX-2 gene and protein expression levels according to treatment of the ethanol extract of *Angelica gigas* Nakai are shown in FIG. 5 (mRNA expression level)

and FIG. 6 (protein expression level), respectively. As shown in FIGS. 5 and 6, no COX-2 mRNA and protein expressions were observed in the normal group (N), whereas both COX-2 mRNA and protein expression levels were greatly increased in the control group (C), but both COX-2 mRNA and protein expression levels were decreased in an *Angelica gigas* Nakai ethanol extract concentration-dependent manner in the *Angelica gigas* Nakai ethanol extract-treated groups (25, 50 and 100 mg/kg).

Figure 7:
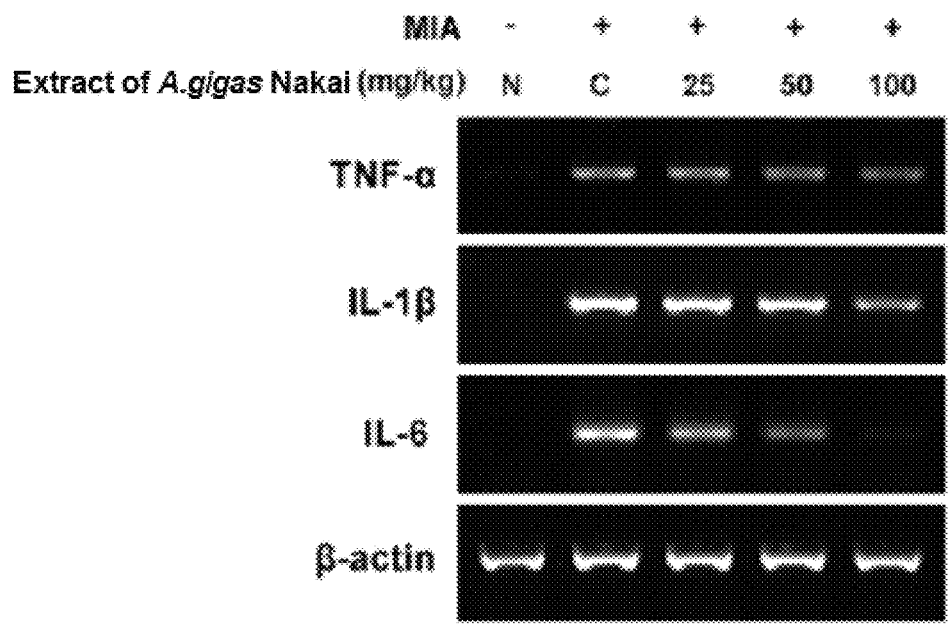
FIG. 7 is RT-PCR results showing changes in TNF-α, IL-1β and IL-6 gene levels in cartilage tissues according to concentrations of the *Angelica gigas* Nakai extract, after treatment of the *Angelica gigas* Nakai extract.

Changes in TNF-α, IL-1β and IL-6 gene expression levels according to treatment of the ethanol extract of *Angelica gigas* Nakai are shown in FIG. 7. As shown in FIG. 7, compared with the normal group (N), all TNF-α, IL-1β and IL-6 mRNA expression levels were greatly increased in the control group (C), but all TNF-α, IL-1β and IL-6 mRNA expression levels were decreased by treatment of the ethanol extract of *Angelica gigas* Nakai.

The results of FIGS. 3 to 7 demonstrated that the ethanol extract of *Angelica gigas* Nakai has the effects of inhibiting gene and protein expressions of inflammation-related factors in the cartilage tissues, thereby greatly decreasing the expression levels thereof.

Figure 17:
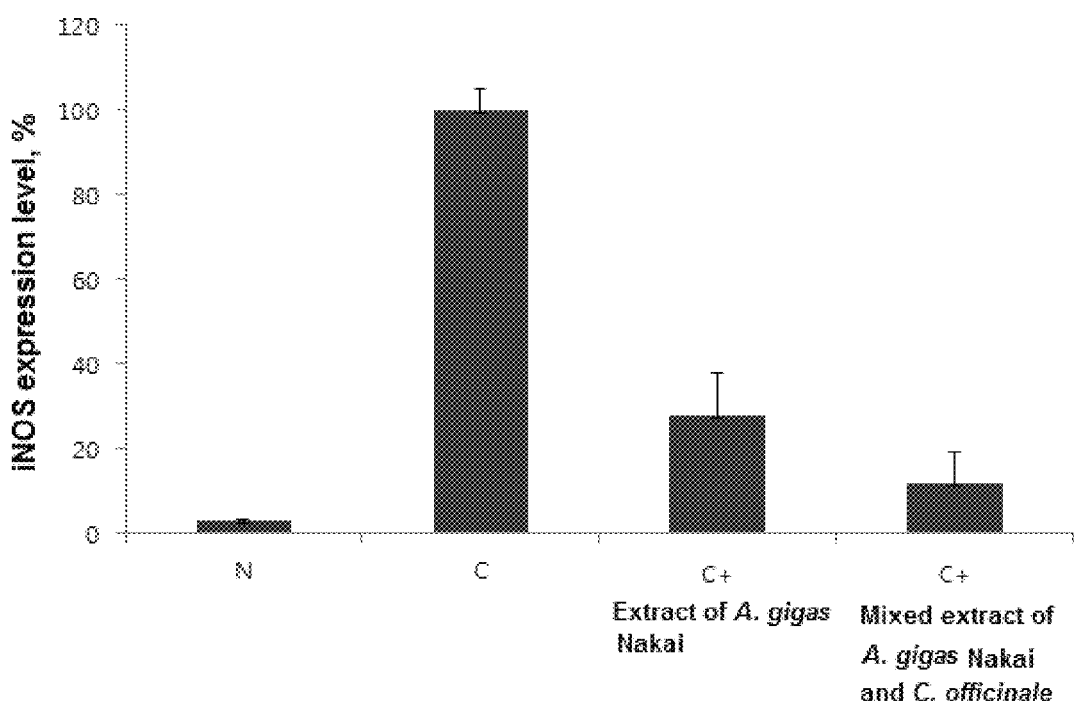
FIG. 17 is a graph showing changes in iNOS mRNA expression levels in the cartilage tissues according to treatment of the extract of *Angelica gigas* Nakai or the mixed extract of *Angelica gigas* Nakai and *Cnidium officinale*.

Further, in order to examine the effects of the mixed extract of *Angelica gigas* Nakai and *Cnidium officinale* on iNOS expression, the experimental animals prepared in Reference Example 1 (the group treated with the ethanol extract powder of *Angelica gigas* Nakai and the group treated with the mixed extract powder of *Angelica gigas* Nakai and *Cnidium officinale*; each administered in an amount of 100 mg/kg) were used to perform RT-PCR for the measurement of iNOS expression levels in the same manner as above, which were quantified and shown in FIG. 17.

In FIG. 17, 'N' represents chondrocytes of a normal white rat, 'C' represents a non-extract-treated group after MIA injection, 'C+*Angelica gigas* Nakai extract powder' represents a group treated with the ethanol extract of *Angelica gigas* Nakai after MIA injection, and 'C+*Angelica gigas* Nakai, *Cnidium officinale* mixed extract' represents a group treated with the mixed extract of *Angelica gigas* Nakai and *Cnidium officinale* after MIA injection. Each value was expressed as a relative value (%), when the iNOS expression level in the 'non-extract-treated group after MIA injection' was taken as 100%. As shown in FIG. 17, the iNOS expression level was remarkably reduced in the cartilage tissues of the group treated with the ethanol extract of *Angelica gigas* Nakai or the group treated with the mixed extract of *Angelica gigas* Nakai and *Cnidium officinale*, as compared with the non-extract-treated group after MIA injection. In particular, a high reduction in the iNOS expression level was observed in the cartilage tissue of the group treated with the mixed extract of *Angelica gigas* Nakai and *Cnidium officinale*.

Example 5: Measurement of TNF-α, IL-1β and IL-6 Contents in Serum

From the blood of experimental animals (the group treated with the ethanol extract of *Angelica gigas* Nakai of Reference Example 1) at 2 days after injection of MIA, serum was separated and the contents of TNF-α, and IL-6 as inflammatory indices were measured using an ELISA assay kit (R&D Systems, Minneapolis, Minn., USA).

Figure 8:
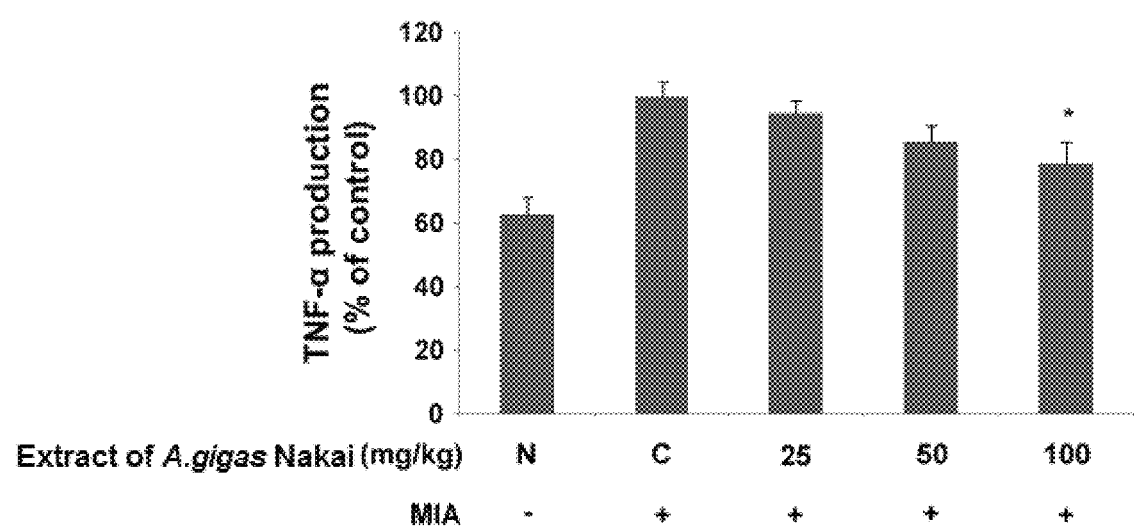
FIG. 8 is a graph showing changes in serum TNF-α level according to administration concentrations of the *Angelica gigas* Nakai extract, after treatment of the *Angelica gigas* Nakai extract.
Figure 9:
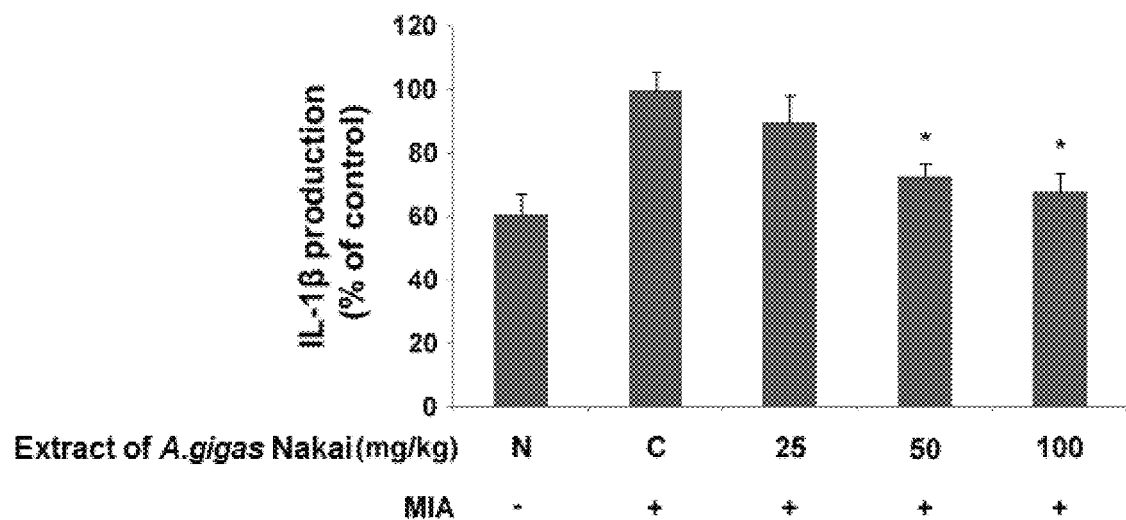
FIG. 9 is a graph showing changes in serum IL-1β level according to administration concentrations of the *Angelica gigas* Nakai extract, after treatment of the *Angelica gigas* Nakai extract.
Figure 10:
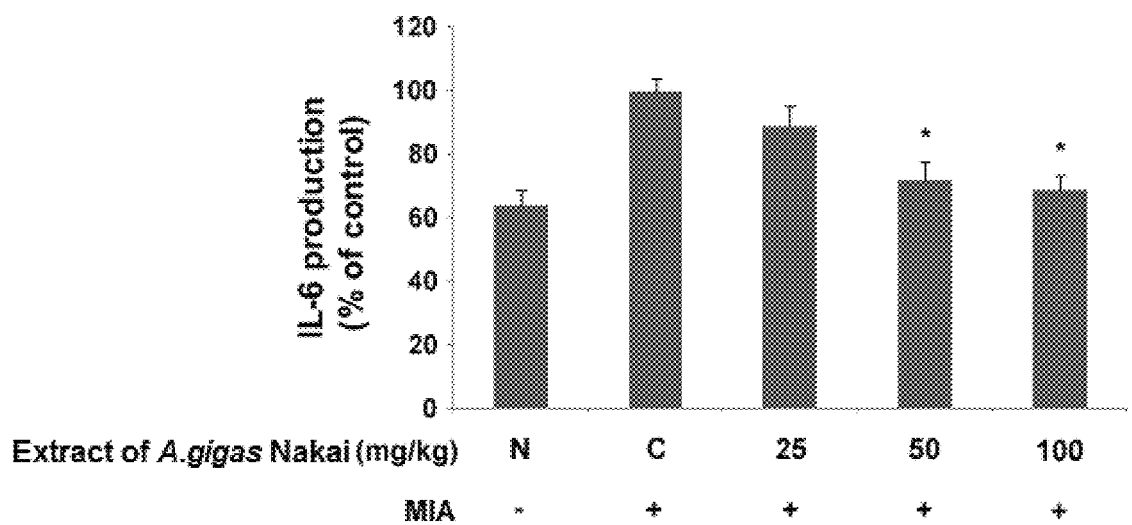
FIG. 10 is a graph showing changes in serum IL-6 level according to administration concentrations of the *Angelica gigas* Nakai extract, after treatment of the *Angelica gigas* Nakai extract.

The obtained results are shown in FIG. 8 (TNF-α content), FIG. 9 (IL-1β content), and FIG. 10 (IL-6 content), respectively. As shown in FIG. 8, when TNF-α content was 100±4.9% in a control (C), it was 95±3.8%, 87.6±5.1%, and 79.2±6.7% in treated groups (25, 50 and 100 mg/kg), respectively, indicating that TNF-α contents in the serum were reduced by administration of the ethanol extract of *Angelica gigas* Nakai. As shown in FIG. 9, when IL-1β content was 100±5.8% in a control, it was 61.2±6.4% in a normal group, and 90.5±8.2%, 73.1±4.1%, and 68.4±6.0% in treated groups (25, 50 and 100 mg/kg), respectively, indicating that IL-1β contents in the serum were reduced by administration of the ethanol extract of *Angelica gigas* Nakai. Further, as shown in FIG. 10, when IL-6 content was 100±3.9% in a control, it was 63.9±4.7% in a normal group, and 89.0±6.5%, 72.6±6.1%, and 69.3±4.2% in treated groups (25, 50 and 100 mg/kg), respectively, indicating that IL-6 contents in the serum were reduced by administration of the extract of *Angelica gigas* Nakai.

The experimental animals (the group treated with the mixed extract of *Angelica gigas* Nakai and *Cnidium officinale* of Reference Example 1: administration dose; 100 mg/kg) at 2 days after injection of MIA were also subjected to the above experiment. The results are shown in FIG. 18 (TNF-alpha expression level; %) and FIG. 19 (IL-1 beta expression level; %), together with the result of the group treated with the ethanol extract of *Angelica gigas* Nakai of Reference Example 1 (administration dose; 100 mg/kg).

Figure 18:
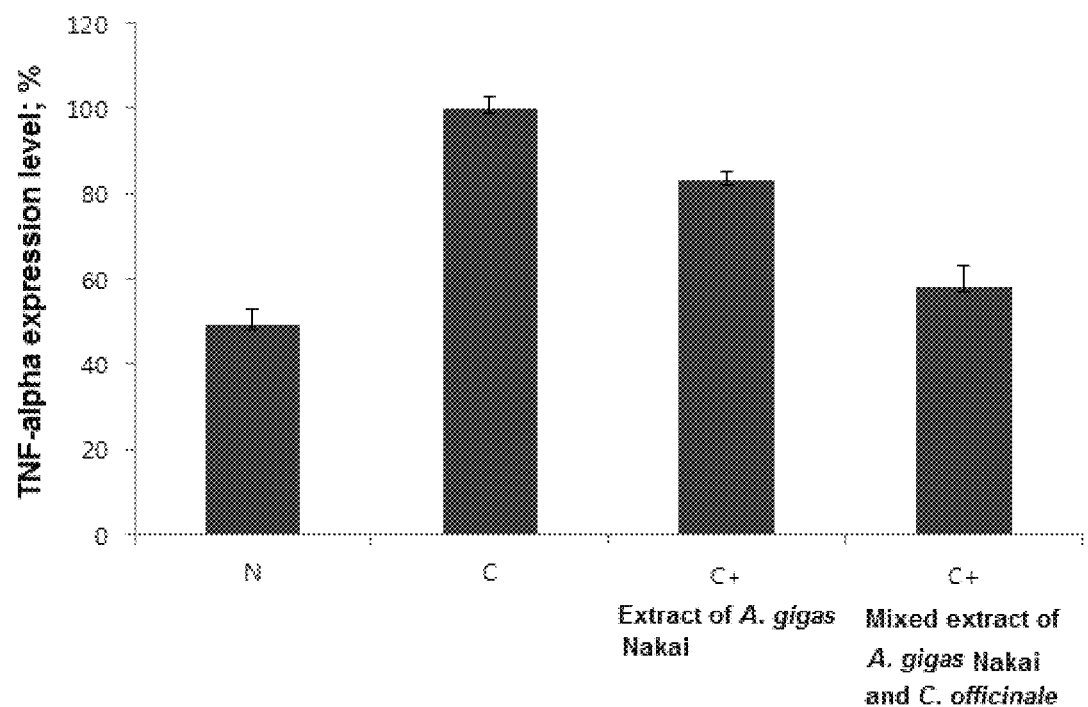
FIG. 18 is a graph showing changes in serum TNF-α contents according to treatment of the extract of *Angelica gigas* Nakai or the mixed extract of *Angelica gigas* Nakai and *Cnidium officinale*.
Figure 19:
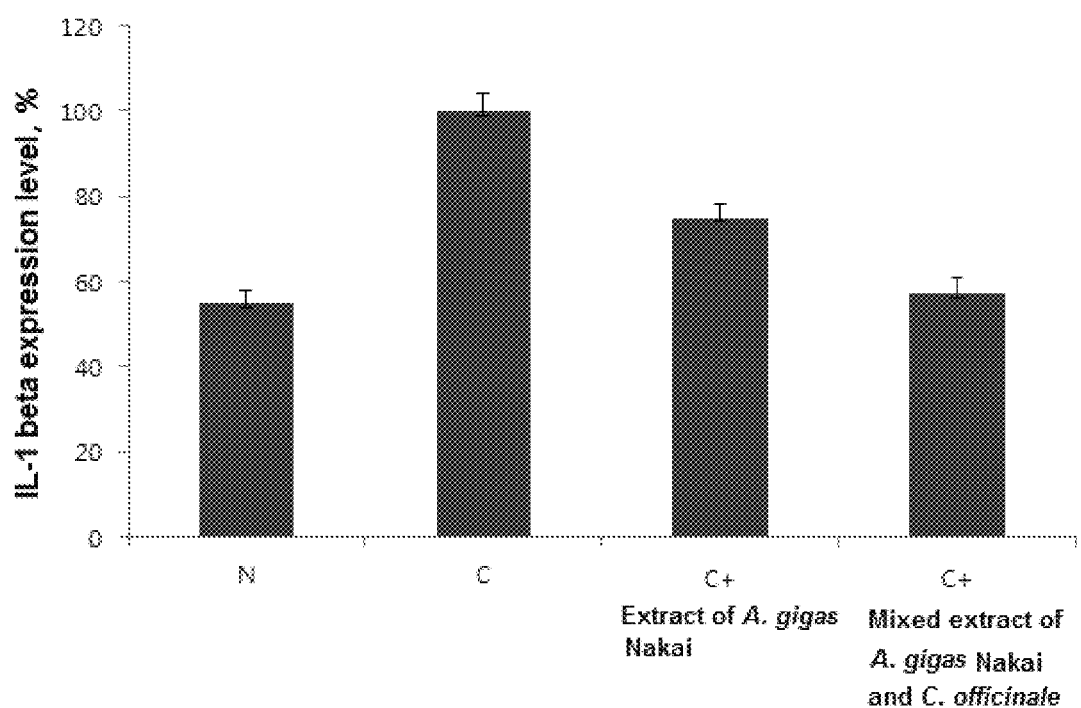
FIG. 19 is a graph showing changes in serum IL-1β levels according to treatment of the extract of *Angelica gigas* Nakai or the mixed extract of *Angelica gigas* Nakai and *Cnidium officinale*.

In FIGS. 18 and 19, 'N' represents the cartilage tissue of a normal white rat, 'C' represents a non-extract-treated group after MIA injection, 'C+*Angelica gigas* Nakai extract powder' represents a group treated with the ethanol extract of *Angelica gigas* Nakai after MIA injection, and 'C+*Angelica gigas* Nakai, *Cnidium officinale* mixed extract' represents a group treated with the mixed extract of *Angelica gigas* Nakai and *Cnidium officinale* after MIA injection. Each value was expressed as a relative value (%), when the TNF-alpha expression level or the IL-1beta expression level in the 'non-extract-treated group after MIA injection' was taken as 100%. As shown in FIGS. 18 and 19, TNF-alpha expression level and IL-1beta expression level were remarkably reduced in the cartilage tissue of the group treated with the ethanol extract of *Angelica gigas* Nakai or the group treated with the mixed extract of *Angelica gigas* Nakai and *Cnidium officinale*, as compared with the non-extract-treated group after MIA injection. In particular, the TNF-alpha expression level and the IL-1beta expression level in the cartilage tissue of the group treated with the mixed extract of *Angelica gigas* Nakai and *Cnidium officinale* were reduced close to those in the normal cartilage tissue.

Example 6: Effects on Matrix Metalloproteinase (MMP) Expression 6.1. Effects of Ethanol Extract of *Angelica gigas* Nakai and Mixed Ethanol Extract of *Angelica gigas* Nakai and *Cnidium officinale* on MMP Expression Matrix metalloproteinases (MMPs) are major proteins involved in the catabolism of cartilage tissues, and of them, MMP-3, MMP-13, etc. are known to show greatly increased expressions and activities in degenerative osteoarthritis.

Accordingly, in the present Example, the effects of the extract of *Angelica gigas* Nakai and the mixed extract of *Angelica gigas* Nakai and *Cnidium officinale* on MMP-3 and MMP-13 expressions were tested.

The knee articular cartilages were removed from the osteoarthritis-induced white rats prepared in Reference Example 3 (the group treated with the ethanol extract powder of *Angelica gigas* Nakai (administration dose: 100 mg/kg) and the group treated with the mixed extract powder of *Angelica gigas* Nakai and *Cnidium officinale* (administration dose: 100 mg/kg)), and ground. Then, from the cartilage tissues, total RNAs were separated using a total RNA extraction kit (iNtRON Biotechnology Inc., Korea). Total RNAs were quantified and each cDNA was synthesized from an equal amount (1 μg) of the total RNA using an RT-PreMix (iNtRON Biotechnology Inc.). Respective primers corresponding to MMP-3 and MMP-13 genes were used to perform RT-PCR under conditions of total 30 cycles of 94° C. 1 min, 50~65° C. 45 sec, and 72° C. 1 min.

```
MMP-3 primer
Forward:
                                      (SEQ ID NO: 13)
GAGTGTGGATTCTGCCATTGAG Reverse:
                                      (SEQ ID NO: 14)
TTATGTCAGCCTCTCCTTCAGAGA MMP-13 primer
Forward:
                                      (SEQ ID NO: 15)
ACGTTCAAGGAATCCAGTCTCTCT Reverse:
                                      (SEQ ID NO: 16)
GGATAGGGCTGGGTCACACTT
```

Figure 20:
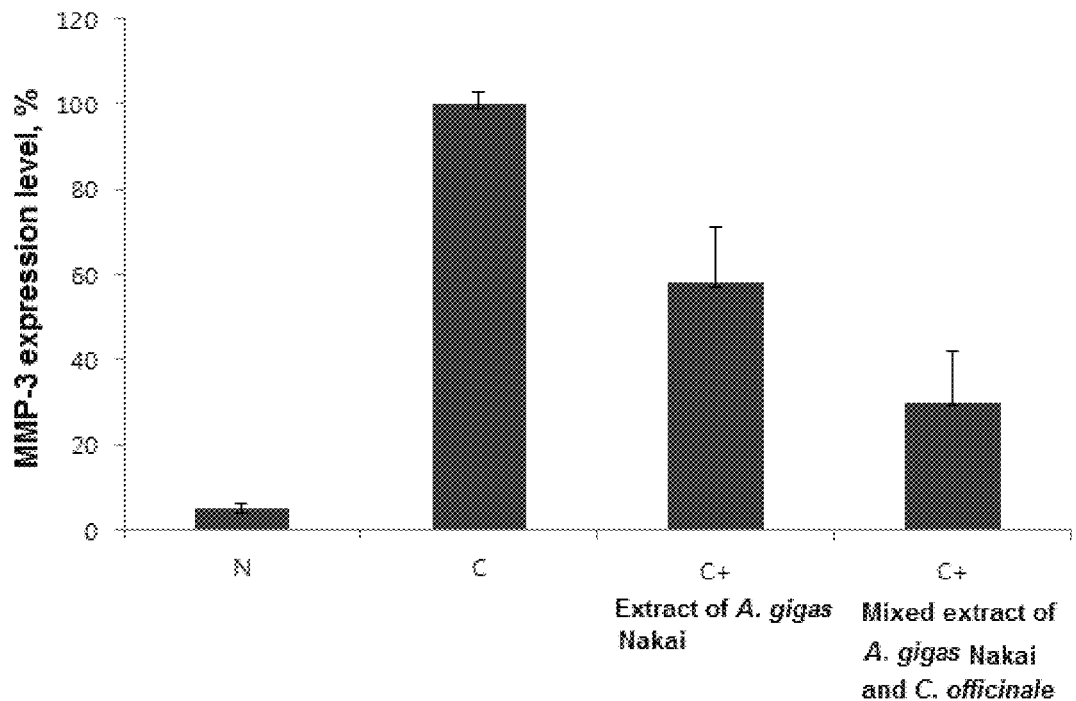
FIG. 20 is a graph showing changes in MMP-3 expression levels according to treatment of the extract of *Angelica gigas* Nakai or the mixed extract of *Angelica gigas* Nakai and *Cnidium officinale*.
Figure 21:
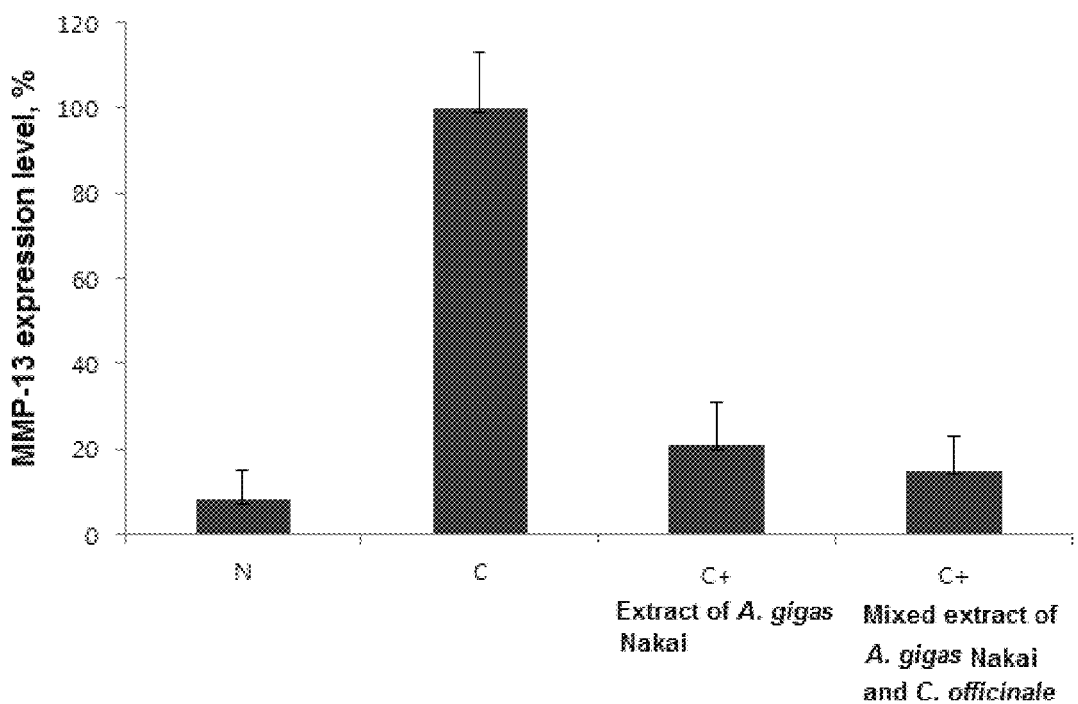
FIG. 21 is a graph showing changes in MMP-13 expression levels according to treatment of the extract of *Angelica gigas* Nakai or the mixed extract of *Angelica gigas* Nakai and *Cnidium officinale*.

The obtained results are shown in FIG. 20 (MMP-3 expression level) and FIG. 21 (MMP-13 expression level). In FIGS. 20 and 21, 'N' represents the cartilage tissue of a normal white rat, 'C' represents a non-extract-treated group after MIA injection, 'C+*Angelica gigas* Nakai extract powder' represents a group treated with the ethanol extract of *Angelica gigas* Nakai after MIA injection, and 'C+*Angelica gigas* Nakai, *Cnidium officinale* mixed extract' represents a group treated with the mixed extract of *Angelica gigas* Nakai and *Cnidium officinale* after MIA injection. Each value was expressed as a relative value (%), when the MMP-3 expression level or MMP-13 expression level in the 'non-extract-treated group after MIA injection' was taken as 100%. As shown in FIGS. 20 and 21, MMP-3 expression level and MMP-13 expression level were remarkably reduced in the cartilage tissue of the group treated with the ethanol extract of *Angelica gigas* Nakai or the group treated with the mixed extract of *Angelica gigas* Nakai and *Cnidium officinale*, as compared with the non-extract-treated group after MIA injection. In particular, more remarkable reductions in MMP-3 expression level and the MMP-13 expression level were observed in the cartilage tissue of the group treated with the mixed extract of *Angelica gigas* Nakai and *Cnidium officinale*.

6.2. Effects of Mixing Ratio of Mixed Extract of *Angelica gigas* Nakai and *Cnidium officinale* on MMP Expression In the same manner as in Example 6.1, the effects of the mixed extract of *Angelica gigas* Nakai and *Cnidium officinale* on MMP-3 and MMP-13 expressions were tested according to a mixing ratio of *Angelica gigas* Nakai and *Cnidium officinale* (administration dose: 100 mg/kg).

Figure 24:
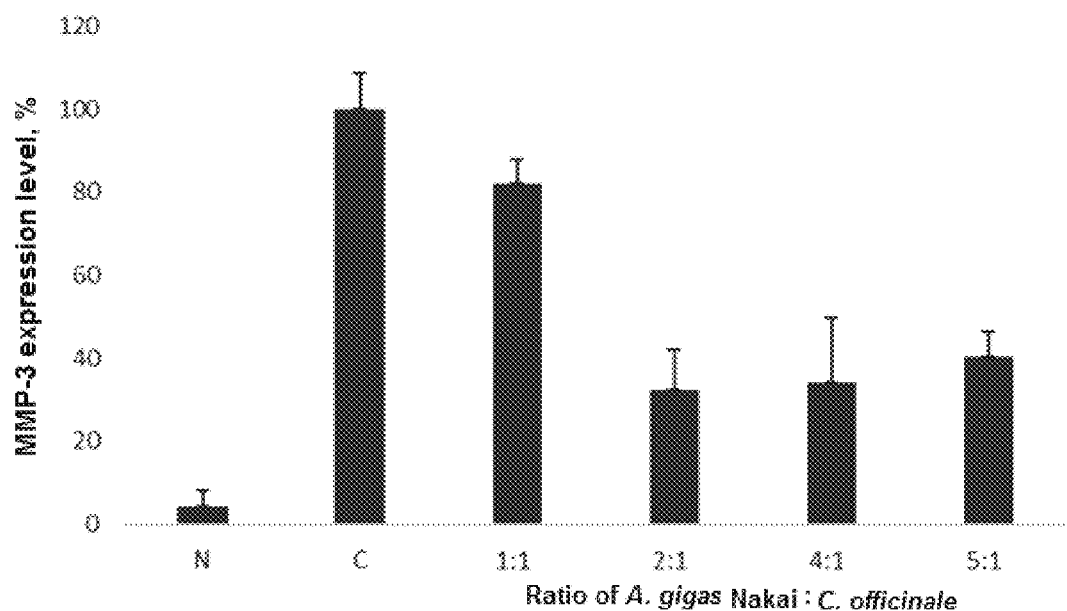
FIG. 24 is a graph showing changes in MMP-3 expression levels according to mixing ratios of the mixed extract of *Angelica gigas* Nakai and *Cnidium officinale*.

The obtained results of MMP-3 expression level are shown in Table 2 and FIG. 24.

TABLE 2

|  | N | C | Angelica gigas Nakai:Cnidium officinale; 1:1 | Angelica gigas Nakai:Cnidium officinale; 2:1 | Angelica gigas Nakai:Cnidium officinale; 4:1 | Angelica gigas Nakai:Cnidium officinale; 5:1 |
|---|---|---|---|---|---|---|
| MMP-3 expression level, % | 4.385 | 100 | 81.9016 | 32.4638 | 34.323 | 40.405 |

Figure 25:
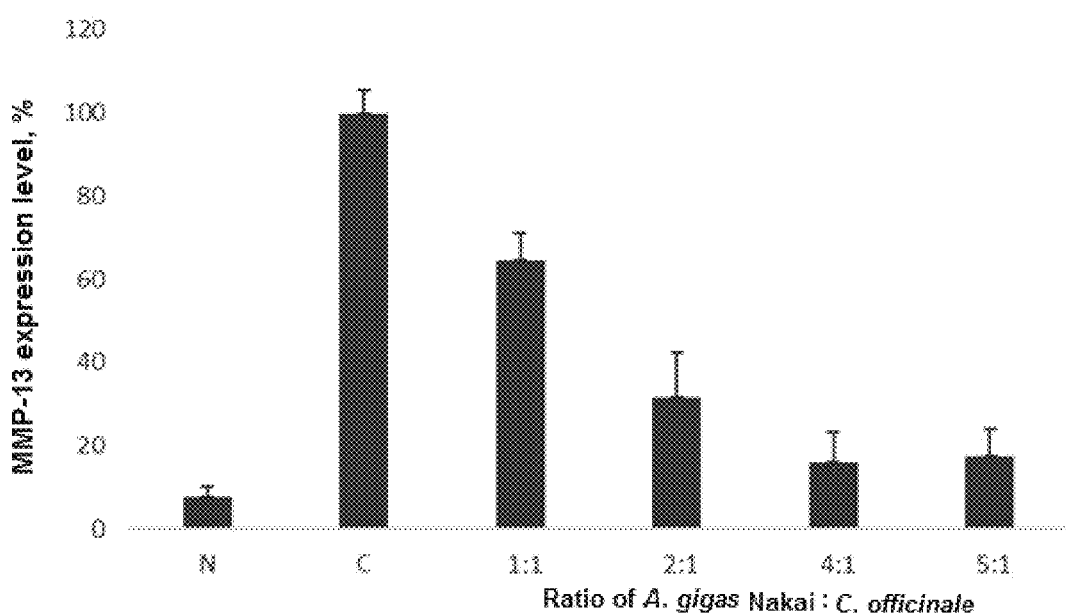
FIG. 25 is a graph showing changes in MMP-13 expression levels according to mixing ratios of the mixed extract of *Angelica gigas* Nakai and *Cnidium officinale*.

The obtained results of MMP-13 expression level are shown in Table 3 and FIG. 25.

TABLE 3

|  | N | C | Angelica gigas Nakai:Cnidium officinale; 1:1 | Angelica gigas Nakai:Cnidium officinale; 2:1 | Angelica gigas Nakai:Cnidium officinale; 4:1 | Angelica gigas Nakai:Cnidium officinale; 5:1 |
|---|---|---|---|---|---|---|
| MMP-13 expression level, % | 7.7918 | 100 | 64.61499 | 31.5445 | 15.848 | 17.4016 |

In Tables 2 and 3, and FIGS. 24 and 25, 'N' represents the cartilage tissue of a normal white rat, and 'C' represents a non-extract-treated group after MIA injection. Each value was expressed as a relative value (%), when the MMP-3 expression level or MMP-13 expression level in the 'non-extract-treated group after MIA injection' was taken as 100%. As shown in Tables 2 and 3, and FIGS. 24 and 25, MMP-3 expression level and MMP-13 expression level were remarkably reduced in the cartilage tissue of the group treated with the mixed extract of *Angelica gigas* Nakai and *Cnidium officinale*, as compared with the non-extract-treated group after MIA injection. In particular, a group treated with 2:1 mixed extract of *Angelica gigas* Nakai and *Cnidium officinale*, a group treated with 4:1 mixed extract of *Angelica gigas* Nakai and *Cnidium officinale*, and a group treated with 5:1 mixed extract of *Angelica gigas* Nakai and *Cnidium officinale* showed higher reductions in MMP-3 expression level and MMP-13 expression level of the cartilage tissues than a group treated with 1:1 mixed extract of *Angelica gigas* Nakai and *Cnidium officinale*.

6.3. Effects of Ethanol Extract and Cold Ethanol Extract on MMP Expression

In the same manner as in Example 6.1, the effects of the ethanol extract of *Angelica gigas* Nakai (Example 1.1) and the mixed ethanol extract of *Angelica gigas* Nakai and *Cnidium officinale* (Example 1.3; mixing ratio of 2:1) on MMP-3 and MMP-13 expressions were tested, and compared with the water extract of *Angelica gigas* Nakai (Comparative Example 1), the cold ethanol extract of *Angelica gigas* Nakai (Comparative Example 3), the mixed water extract of *Angelica gigas* Nakai and *Cnidium officinale* (Comparative Example 2), and the mixed cold ethanol extract of *Angelica gigas* Nakai and *Cnidium officinale* (Comparative Example 4) (administration dose: 100 mg/kg).

The obtained results of MMP-3 expression level (%) are shown in the following Table 4 and FIG. 28.

Figure 28:
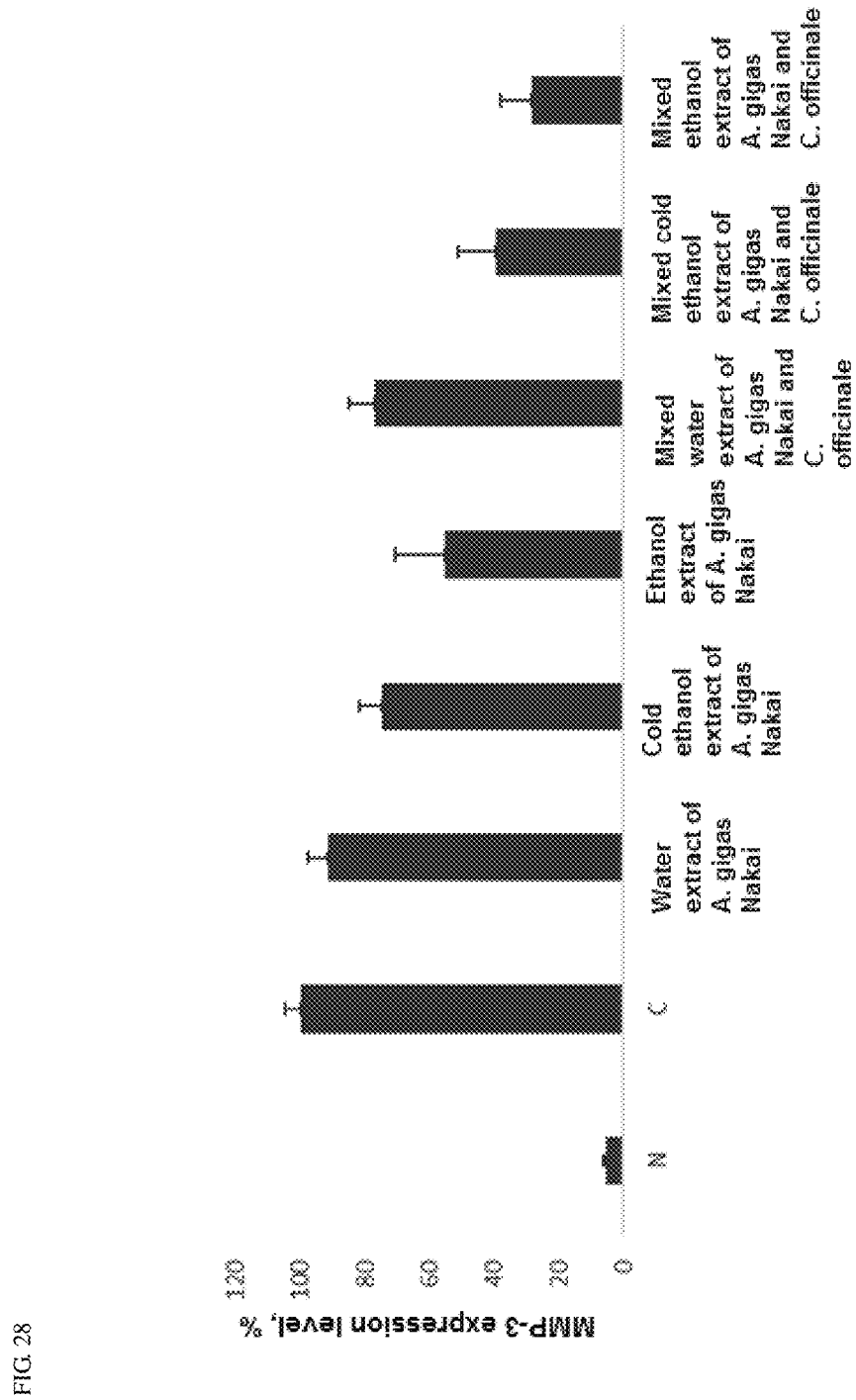
FIG. 28 is a graph showing changes in MMP-3 expression levels according to treatment of an ethanol extract or a cold ethanol extract.
Figure 29:
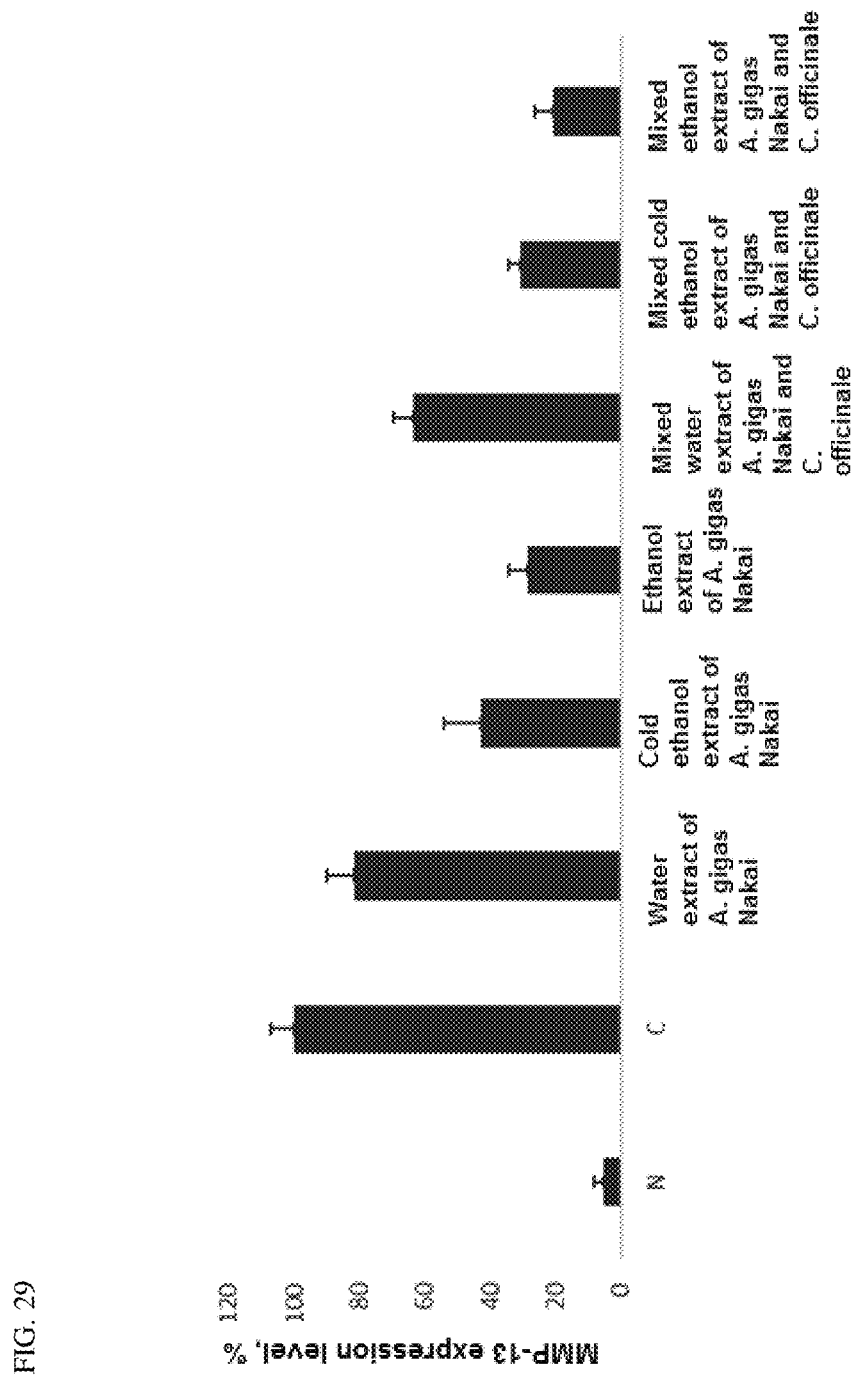
FIG. 29 is a graph showing changes in MMP-13 expression levels according to treatment of the ethanol extract or the cold ethanol extract.

In Tables 4 and 5, and FIGS. 28 and 29, 'N' represents the cartilage tissue of a normal white rat, and 'C' represents a non-extract-treated group after MIA injection. Each value was expressed as a relative value (%), when the MMP-3 expression level or MMP-13 expression level in the 'non-extract-treated group after MIA injection' was taken as 100%. As shown in Tables 4 and 5, and FIGS. 28 and 29, MMP-3 expression level and MMP-13 expression level were remarkably reduced in the cartilage tissues of the group treated with the ethanol extract of *Angelica gigas* Nakai and the mixed ethanol extract of *Angelica gigas* Nakai and *Cnidium officinale*, as compared with the non-extract-treated group after MIA injection, the group treated with the water extract of *Angelica gigas* Nakai, the group treated with the cold ethanol extract of *Angelica gigas* Nakai, the group treated with the mixed water extract of *Angelica gigas* Nakai and *Cnidium officinale*, and the group treated with the mixed cold ethanol extract of *Angelica gigas* Nakai and *Cnidium officinale*.

Example 7: Measurement of Body Weight

The body weights of the experimental animals (the group treated with the ethanol extract powder of *Angelica gigas* Nakai) prepared in Reference Example 3 were measured on the day of experiment, 4, 8, 12, 16, and 20 days. The obtained results are shown in the following FIG. 11. As shown in FIG. 11, the control group showed a significant reduction in the rate of increase of body weight from the $12^{th}$ day of experiment to the $20^{th}$ day of experiment, as compared with the normal group. The treated group showed a high body weight from the $8^{th}$ day of experiment to the $20^{th}$ day of experiment, as compared with the control group, and a significant increase in the body weight from the $16^{th}$ day of experiment, as compared with the control group. These results suggest that the ethanol extract of *Angelica gigas* Nakai has no harmful effect on the body of experimental animals.

TABLE 4

|  | N | C | Water extract of *Angelica gigas* Nakai | Cold ethanol extract of *Angelica gigas* Nakai | Ethanol extract of *Angelica gigas* Nakai | Mixed water extract of *Angelica gigas* Nakai and *Cnidium officinale* | Mixed cold ethanol extract of *Angelica gigas* Nakai and *Cnidium officinale* | Mixed ethanol extract of *Angelica gigas* Nakai and *Cnidium officinale* |
|---|---|---|---|---|---|---|---|---|
| MMP-3 | 5.35289 | 100 | 91.6314 | 74.8041 | 55.3586 | 77.0822 | 39.5443 | 28.4804 |

The obtained results of MMP-13 expression level (%) are shown in the following Table 5 and FIG. 29.

TABLE 5

|  | N | C | Water extract of *Angelica gigas* Nakai | Cold ethanol extract of *Angelica gigas* Nakai | Ethanol extract of *Angelica gigas* Nakai | Water extract of *Angelica gigas* Nakai and *Cnidium officinale* | Cold ethanol extract of *Angelica gigas* Nakai and *Cnidium officinale* | Mixed ethanol extract of *Angelica gigas* Nakai and *Cnidium officinale* |
|---|---|---|---|---|---|---|---|---|
| MMP-13 | 4.9827 | 100 | 81.3088 | 42.5082 | 28.3135 | 63.4666 | 30.6137 | 20.5336 |

Example 8: Measurement of Glycosaminoglycan (GAG) Content in Synovial Fluid of Knee Joint 8.1. Effects of Ethanol Extract of *Angelica gigas* Nakai and Mixed Ethanol Extract of *Angelica gigas* Nakai and *Cnidium officinale* on GAG Content in Synovial Fluid of Knee Joint GAG loss in the articular cartilage and progression of osteoarthritis may be indirectly detected by measuring the contents of GAG released into the synovial fluid due to osteoarthritis.

GAG contents in the synovial fluid of knee joint were measured by DMMB (1,9-dimethylmethylene blue) assay using a sulfated glycosaminoglycan assay kit (Biocolor, UK; Blyscan™).

MIA was injected into the experimental animals (the group treated with ethanol extract powder of *Angelica gigas* Nakai) prepared in Reference Example 3, and then the synovial fluids of knee joints were collected therefrom at 3 weeks. A dye (DMMB) was added to each of the synovial fluids and allowed to react for 30 minutes, followed by centrifugation at 12,000 rpm for 10 minutes. Thereafter, an unreacted dye-containing supernatant was removed to obtain GAG-dye complexes, to which 0.5 mL of a dissociation solution was added to dissolve the GAG-dye complexes, and then centrifuged at 12,000 rpm for 5 minutes to obtain samples.

Each 200 µL (microliter) of the supernatants of the samples was added to a 96-well plate, and absorbance at 656 nm was measured using an ELISA reader (Molecular Devices, Sunnyvale, USA). The GAG content in each sample was calculated from a standard calibration curve of bovine chondroitin sulfate used as a standard material (n=8).

Figure 12:
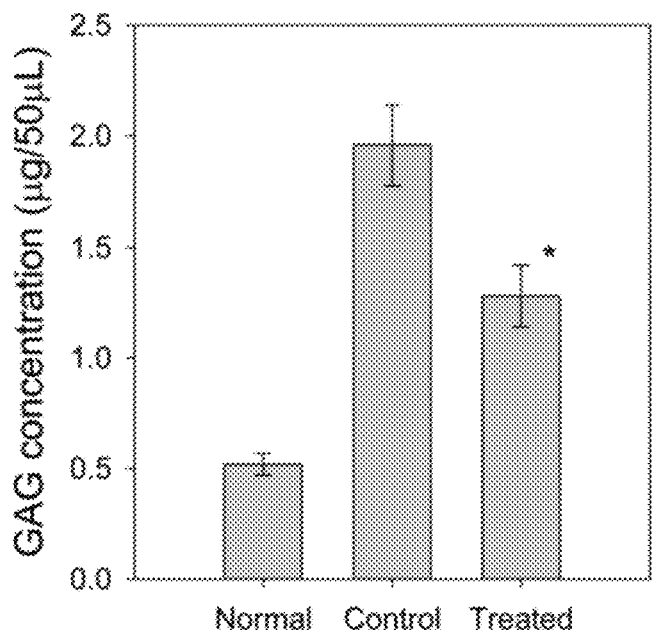
FIG. 12 is a graph showing a comparison of glycosaminoglycan (GAG) contents in the synovial fluids of knee joints between *Angelica gigas* Nakai extract-treated experimental animals and control and normal groups.

The obtained results are shown in FIG. 12. As shown in FIG. 12, the GAG content in the synovial fluid of knee joint was significantly increased in the control group and the treated groups, compared with the normal group, indicating that GAG present in the articular cartilage is released into the synovial fluid by MIA-induced osteoarthritis. However, it was confirmed that GAG contents in the treated groups were significantly reduced, compared with the control group. This result suggests that the ethanol extract of *Angelica gigas* Nakai inhibits GAG loss in the articular cartilage.

The same experiment was also performed with respect to the group treated with the mixed extract powder of *Angelica gigas* Nakai and *Cnidium officinale* and the group treated with the water extract of *Angelica gigas* Nakai prepared in Reference Example 3.

The obtained results (mean values after the experiment was performed in triplicate) are shown in the following Table 6 and FIG. 22.

TABLE 6

|  | N | C | C + *Angelica gigas* Nakai water extract-treated group | C + *Angelica gigas* Nakai ethanol extract-treated group | C + *Angelica gigas* Nakai and *Cnidium officinale* mixed extract-treated group |
| --- | --- | --- | --- | --- | --- |
| GAG concentration in synovial fluid (µg/50 µL) | 0.513611 | 2.150499 | 1.886145 | 1.266347 | 0.966823 |

Figure 22:
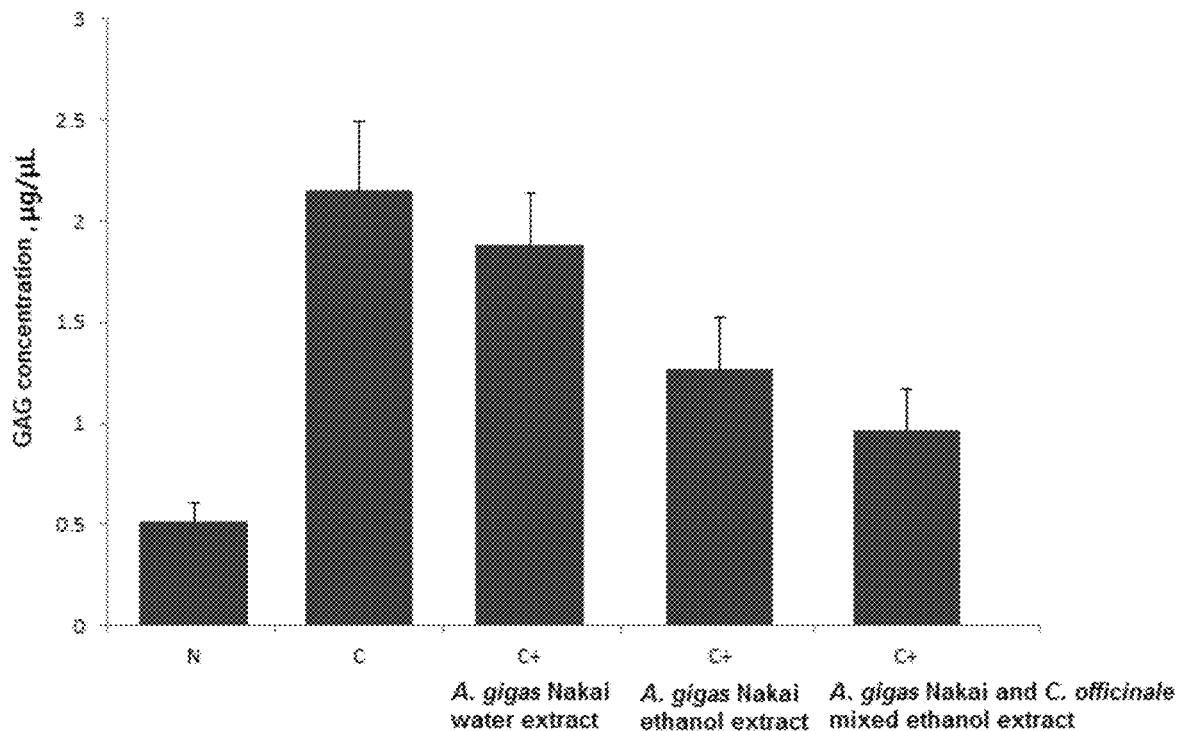
FIG. 22 is a graph showing changes in GAG contents in the synovial fluids of knee joints according to treatment of the extract of *Angelica gigas* Nakai or the mixed extract of *Angelica gigas* Nakai and *Cnidium officinale*.

In Table 6 and FIG. 22, 'N' represents the cartilage tissue of a normal white rat, and 'C' represents a white rat with MIA-induced osteoarthritis. As shown in Table 6 and FIG. 22, when the osteoarthritis-induced white rats were administered with the ethanol extract of *Angelica gigas* Nakai or the mixed extract of *Angelica gigas* Nakai and *Cnidium officinale*, GAG loss was inhibited. In particular, treatment of the ethanol extract of *Angelica gigas* Nakai and treatment of the mixed extract of *Angelica gigas* Nakai and *Cnidium officinale* showed excellent inhibitory effect on GAG, even compared with treatment of the water extract of *Angelica gigas* Nakai ($P<0.01$).

8.2. Effects of Mixing Ratio of Mixed Extract of *Angelica gigas* Nakai and *Cnidium officinale* on GAG Content in Synovial Fluid of Knee Joint In the same manner as in Example 8.1, the effects (inhibitory effect on GAG loss in the articular cartilage) of mixing ratios of the mixed extract of *Angelica gigas* Nakai and *Cnidium officinale* (Example 1.3) on the GAG concentrations in the synovial fluid were tested. The obtained results (GAG concentrations in the synovial fluid) are shown in the following Table 7 and FIG. 26.

TABLE 7

|  | N | C | *Angelica gigas* Nakai:*Cnidium officinale*; 1:1 | *Angelica gigas* Nakai:*Cnidium officinale*; 2:1 | *Angelica gigas* Nakai:*Cnidium officinale*; 4:1 | *Angelica gigas* Nakai:*Cnidium officinale*; 5:1 |
| --- | --- | --- | --- | --- | --- | --- |
| GAG concentration in synovial fluid, µg/µL | 0.5713 | 2.0702 | 1.8386 | 0.9456 | 1.1263 | 1.1018 |

Figure 26:
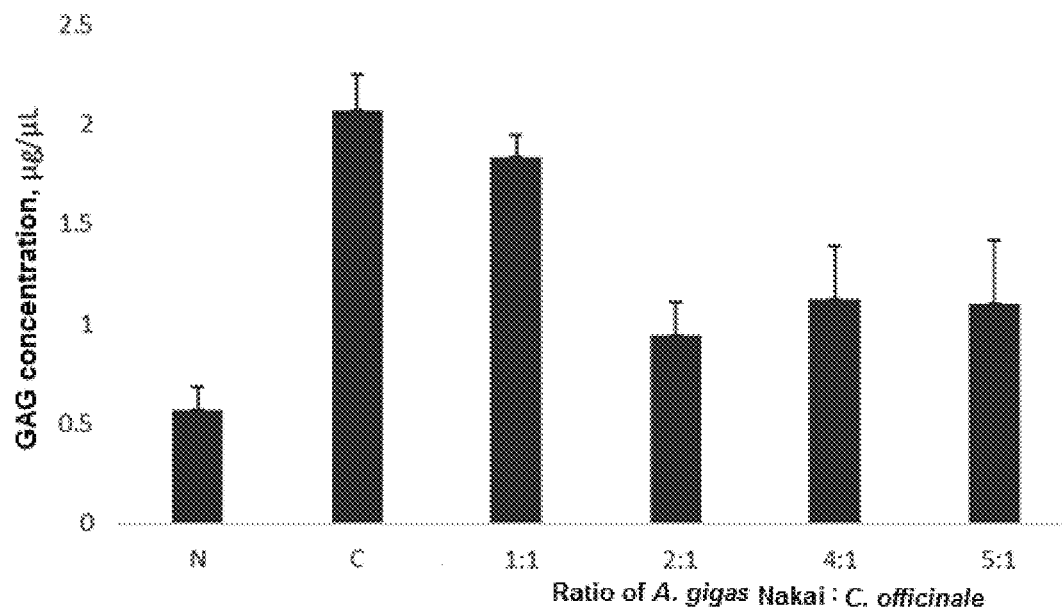
FIG. 26 is a graph showing changes in GAG contents in the synovial fluids of knee joints according to mixing ratios of the mixed extract of *Angelica gigas* Nakai and *Cnidium officinale*.

In Table 7 and FIG. 26, 'N' represents the cartilage tissue of a normal white rat, and 'C' represents a white rat with MIA-induced osteoarthritis. As shown in Table 7 and FIG. 26, GAG concentrations in the synovial fluid were significantly reduced in the groups treated with a 1:1 mixed extract, a 2:1 mixed extract, a 4:1 mixed extract, and a 5:1 mixed extract (Example 1.3) of *Angelica gigas* Nakai and *Cnidium officinale*, compared with the non-extract-treated group after MIA injection and the group treated with the extract of *Angelica gigas* Nakai. In particular, treatment of the 2:1 mixed extract, the 4:1 mixed extract, or the 5:1 mixed extract of *Angelica gigas* Nakai and *Cnidium officinale* showed lower GAG concentrations in the synovial fluid than treatment of the 1:1 mixed extract of *Angelica gigas* Nakai and *Cnidium officinale*. The reduced GAG concentrations in the synovial fluid indicate excellent inhibitory effect on GAG loss in the articular cartilage.

8.3. Effects of Ethanol Extract and Cold Ethanol Extract on GAG Content in Synovial Fluid of Knee Joint In the same manner as in Example 8.1, the effects (inhibitory effect on GAG loss in the articular cartilage) of the ethanol extract of *Angelica gigas* Nakai (Example 1.1) and the mixed ethanol extract of the *Angelica gigas* Nakai and *Cnidium officinale* (Example 1.3; a mixing ratio of 2:1) on the GAG concentrations in the synovial fluid were tested, and compared with the water extract of *Angelica gigas* Nakai (Comparative Example 1), cold ethanol extract of *Angelica gigas* Nakai (Comparative Example 3), the mixed water extract of *Angelica gigas* Nakai and *Cnidium officinale* (Comparative Example 2), and the mixed cold ethanol extract of *Angelica gigas* Nakai and *Cnidium officinale* (Comparative Example 4) (administration dose: 100 mg/kg). The obtained results (GAG concentrations in the synovial fluid) are shown in the following Table 8 and FIG. 30.

indicate that the mixed extract of the above mixing ratio has excellent inhibitory effect on GAG loss in the articular cartilage.

Example 9: Measurement of Tumor Necrosis Factor (TNF-α) Content in Synovial Fluid of Knee Joint The amount of TNF-α in the synovial fluid of knee joint were measured by using a Rat TNF-α ELISA kit (Invitrogen, Camarillo, USA). The experimental animals prepared in Reference Example 3 were injected with MIA, and at 3 weeks, the synovial fluids of knee joints were collected. The collected synovial fluid was diluted with an incubation buffer at a ratio of 1:2, and then 100 μL thereof was added to a well-plate and allowed to react at room temperature for 2 hours to remove a supernatant. After washing 4 times, the plate was reacted with 100 μL of biotin conjugate (Invitrogen, Camarillo, USA) for 1 hour. After washing 4 times, the plate was reacted with 100 μL of Streptavidin-HRP (Invitrogen, Camarillo, USA) for 30 minutes. After washing 4 times, the plate was reacted with a tetramethylbenzidine (TMB) solution for 30 minutes, and thus color was developed. A stop solution was added thereto to stop the reaction. Absorbance of the obtained reaction solution was measured at 450 nm using an ELISA reader (Molecular Devices, Sunnyvale, USA). TNF-α contents in the synovial fluid were measured by using a calibration curve which was obtained from the absorbance range (0.05~3.29) at 450 nm of 8 serially diluted TNF-α standard solutions in a concentration range of 0~750 pg/mL (0, 11.7, 23.4, 46.9, 93.8, 187.5, 375, 750 pg/mL) (n=8).

Figure 13:
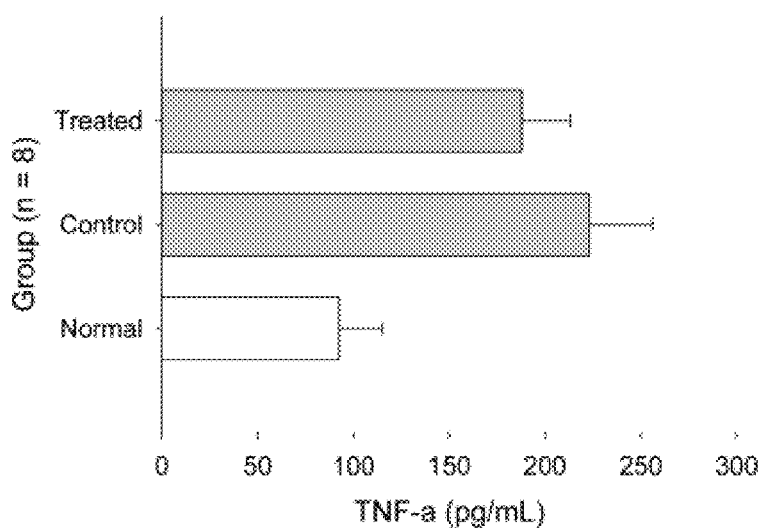
FIG. 13 is a graph showing a comparison of tumor necrosis factor (TNF-α) contents in the synovial fluids of knee joints between *Angelica gigas* Nakai extract-treated experimental animals and control and normal groups.

The obtained results are shown in FIG. 13. As shown in FIG. 13, the TNF-α content in the synovial fluid collected from knee joint was twice higher in the MIA-treated control

TABLE 8

| | N | C | Water extract of *Angelica gigas* Nakai | Cold ethanol extract of *Angelica gigas* Nakai | Ethanol extract of *Angelica gigas* Nakai | Mixed water extract of *Angelica gigas* Nakai and *Cnidium officinale* | Mixed cold ethanol extract of *Angelica gigas* Nakai and *Cnidium officinale* | Mixed ethanol extract of *Angelica gigas* Nakai and *Cnidium officinale* |
|---|---|---|---|---|---|---|---|---|
| GAG concentration in synovial fluid, μg/μL | 0.5801 | 2.2275 | 1.9747 | 1.4716 | 1.21 | 1.5928 | 1.352 | 1.0078 |

Figure 30:
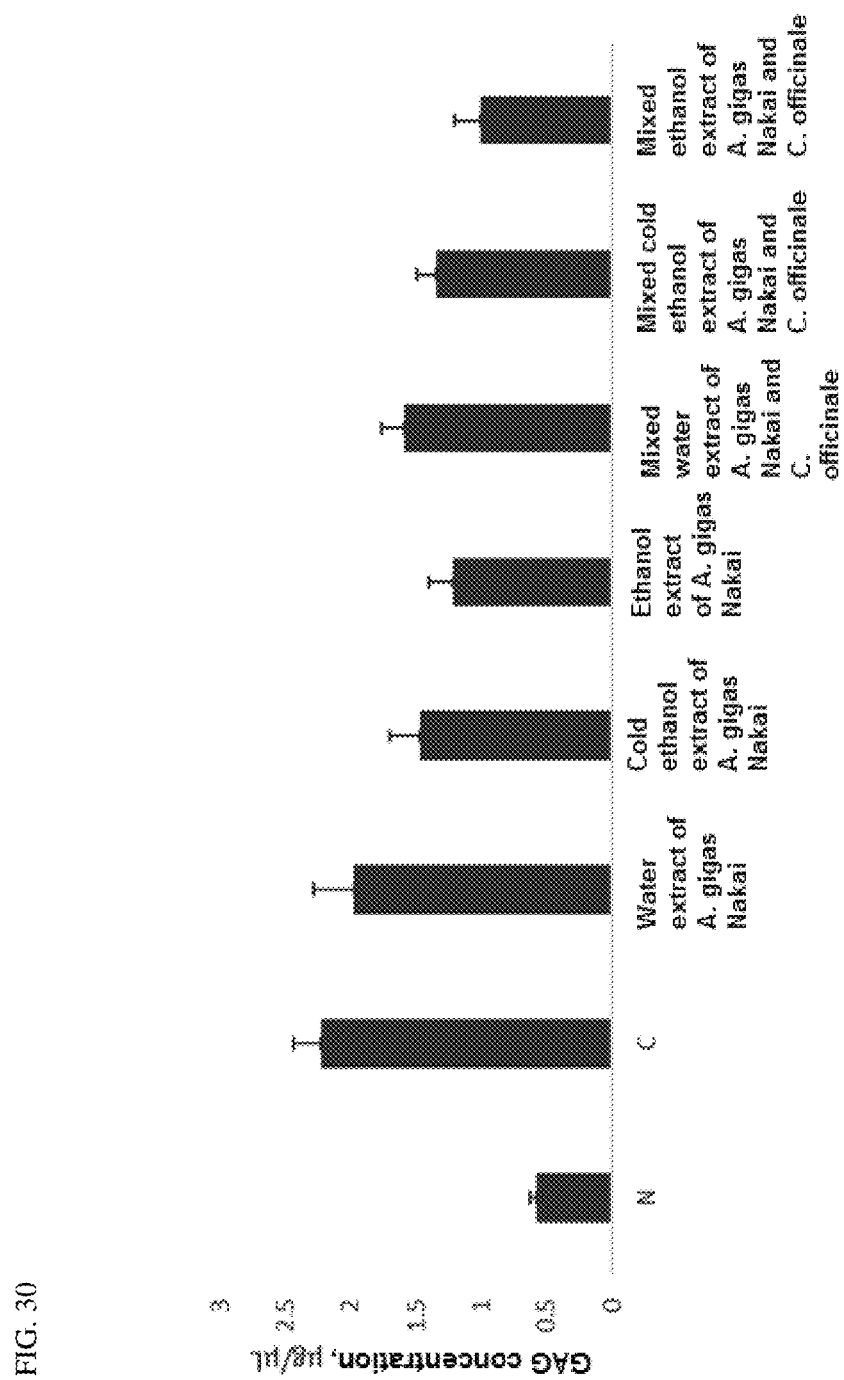
FIG. 30 is a graph showing changes in GAG contents in the synovial fluids of knee joints according to treatment of the ethanol extract or the cold ethanol extract.

In Table 8 and FIG. 30, 'N' represents the cartilage tissue of a normal white rat, and 'C' represents a white rat with MIA-induced osteoarthritis. As shown in Table 8 and FIG. 30, GAG concentrations in the synovial fluid were significantly reduced in the group treated with the ethanol extract of *Angelica gigas* Nakai (Example 1.1) and the group treated with the mixed ethanol extract (Example 1.3; a mixing ratio of 2:1) of *Angelica gigas* Nakai and *Cnidium officinale*, compared with the non-extract-treated group after MIA injection, and the groups treated with the water extract of *Angelica gigas* Nakai (Comparative Example 1), the cold ethanol extract of *Angelica gigas* Nakai (Comparative Example 3), the mixed water extract of *Angelica gigas* Nakai and *Cnidium officinale* (Comparative Example 2), and the mixed cold ethanol extract of *Angelica gigas* Nakai and *Cnidium officinale* (Comparative Example 4). These results group than the normal group, whereas the TNF-α content was lower in the group treated with the ethanol extract of *Angelica gigas* Nakai than in the control group.

Example 10: Measurement of Proteoglycan (PG) Content in Articular Cartilage 10.1. Effects of Ethanol Extract of *Angelica gigas* Nakai and Mixed Ethanol Extract of *Angelica gigas* Nakai and *Cnidium officinale* on PG Content in Articular Cartilage The experimental animals (the group treated with the ethanol extract of *Angelica gigas* Nakai) prepared in Reference Example 3 were injected with MIA, and at 3 weeks, all the experimental animals were lightly anesthetized with ether, and left femur and tibia were removed. The removed knee joint cavity was washed by injecting 0.5 mL of physiological saline thereto. 250 μL or more of the washed synovial fluid was collected, and stored frozen at −80° C.

until testing. Immediately after removing, the right knee joint was fixed in a 10% neutral formalin solution for 24 hours, and the solution was exchanged with 10% formic acid at 24-hr intervals for 72 hours for decalcification. Paraffin blocks were prepared using an automated embedder (Tissue-Tex 4701, Sakura Co., Japan). The prepared paraffin blocks were serially sectioned using a rotary microtome 2040 (Sakura Co., Japan) in a thickness of 5 μm in a vertical direction, and passed through a water bath and a slide warmer, and the sections were attached to slides.

In order to examine PG denaturation of the articular cartilage, the prepared tissue slides were subjected to Safranin-O staining of using the principle of reacting with a sulfur group of a glycoprotein as a substrate. The thin sliced tissue sections were subjected to deparaffinization and hydration processes, and then stained with a Weigert's iron hematoxylin (Sigma, St. Louis, USA) solution for about 10 minutes, and then washed, followed by staining with a 0.02% fast green (FCF) (Sigma, St. Louis, USA) solution for 5 minutes. Subsequently, the tissue sections were stained with 0.1% acetic acid, 0.1% Safranin-O (Sigma, St. Louis, USA) solution, followed by washing.

Staining intensity (average permeability) of the stained tissue sections (articular cartilage) was measured using a color image analyzer (Media Cybernetics, Image-Proplus, USA). Safranin-O staining intensity of each group measured by the color image analyzer was evaluated as a proteoglycan (PG) content ratio in the articular cartilage. An average of the average permeability which was measured in the normal group was taken as 100%, and the average permeabilities of the control group and the treated group were converted to evaluate the PG content ratio (n=8).

Figure 14:
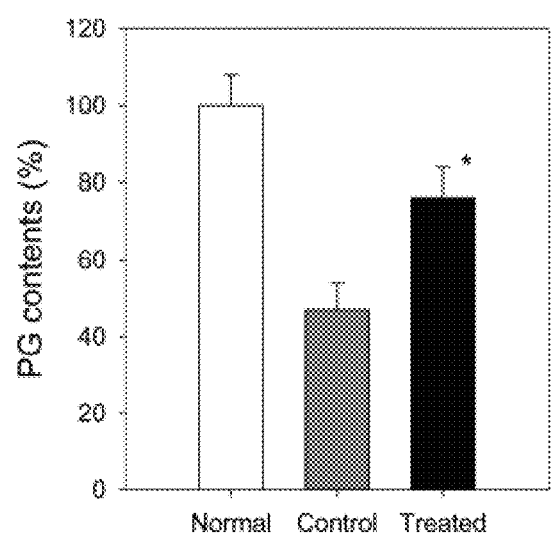
FIG. 14 is a graph showing a comparison of proteoglycan (PG) contents in the articular cartilage tissues between *Angelica gigas* Nakai extract-treated experimental animals and control and normal groups.

The obtained results (PG content ratio in articular cartilage tissue) were shown in FIG. 14. As shown in FIG. 14, the PG content ratio in the articular cartilage tissue was reduced in both the control and treated groups, compared with the normal group, but the PG content ratio in the treated group was significantly less reduced than that in the control group, indicating that the ethanol extract of *Angelica gigas* Nakai significantly inhibits PG destruction in the articular cartilage.

The above same experiment was also performed with respect to the group treated with the mixed extract powder of *Angelica gigas* Nakai and *Cnidium officinale* and the group treated with the water extract of *Angelica gigas* Nakai prepared in Reference Example 3.

The obtained results (mean values after the experiment was performed in triplicate) are shown in the following Table 9 and FIG. 23.

TABLE 9

|  | N | C | C + *Angelica gigas* Nakai water extract-treated group | C + *Angelica gigas* Nakai ethanol extract-treated group | C + *Angelica gigas* Nakai and *Cnidium officinale* mixed extract-treated group |
|---|---|---|---|---|---|
| PG content ratio (%) | 100 | 42.78697 | 64.70708 | 77.16863 | 85.4988 |

Figure 23:
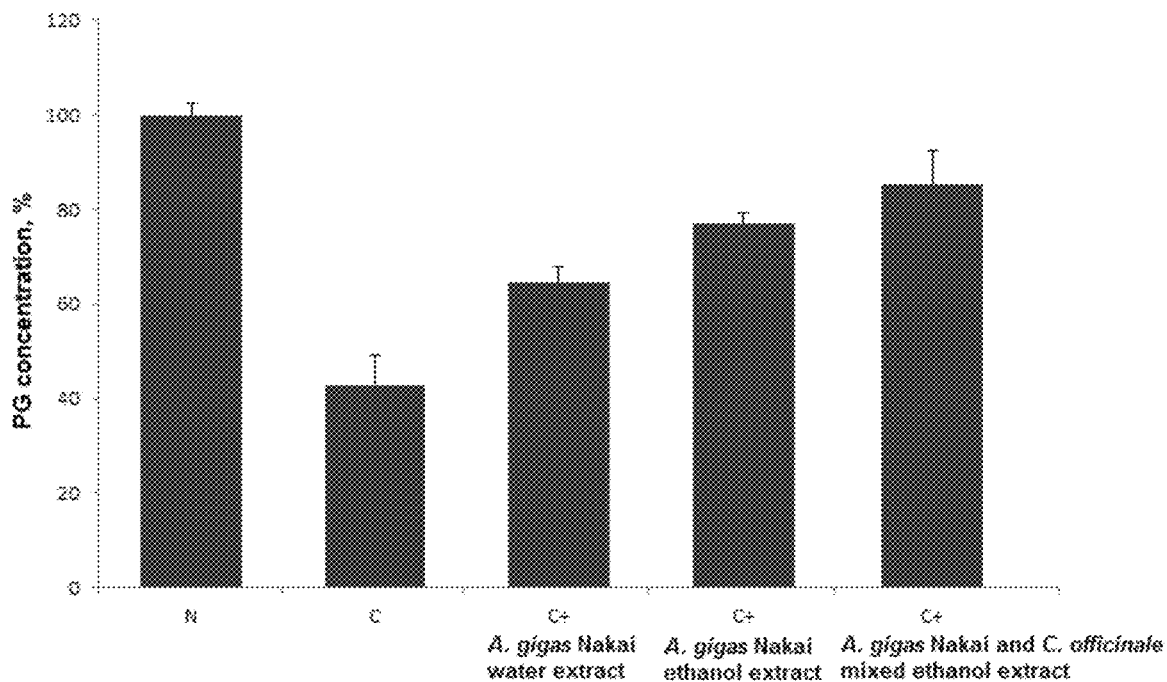
FIG. 23 is a graph showing changes in PG contents in the articular cartilage according to treatment of the extract of *Angelica gigas* Nakai or the mixed extract of *Angelica gigas* Nakai and *Cnidium officinale*.

As shown in Table 9 and FIG. 23, 'N' represents the cartilage tissue of a normal white rat, and 'C' represents a white rat with MIA-induced osteoarthritis. As shown in Table 9 and FIG. 23, when osteoarthritis-induced white rats were administered with the ethanol extract of *Angelica gigas* Nakai or the mixed extract of *Angelica gigas* Nakai and *Cnidium officinale*, PG destruction in the articular cartilage was inhibited. In particular, treatment of the ethanol extract of *Angelica gigas* Nakai and treatment of the mixed extract of *Angelica gigas* Nakai and *Cnidium officinale* showed excellent inhibitory effect on PG destruction, compared with treatment of the water extract of *Angelica gigas* Nakai ($P<0.01$).

10.2. Effects of Mixing Ratio of Mixed Extract of *Angelica gigas* Nakai and *Cnidium officinale* on PG Content in Articular Cartilage In the same manner as in Example 10.1, the inhibitory effects (measured by the PG content ratio in the articular cartilage tissue) of mixing ratios of the mixed extract of *Angelica gigas* Nakai and *Cnidium officinale* (Example 1.3) on PG destruction were tested.

The obtained results (PG content ratio in the articular cartilage tissue) are shown in the following Table 10 and FIG. 27.

TABLE 10

|  | N | C | *Angelica gigas* Nakai:*Cnidium officinale*; 1:1 | *Angelica gigas* Nakai:*Cnidium officinale*; 2:1 | *Angelica gigas* Nakai:*Cnidium officinale*; 4:1 | *Angelica gigas* Nakai:*Cnidium officinale*; 5:1 |
|---|---|---|---|---|---|---|
| PG concentration, % | 98.9246 | 41.2661 | 50.2794 | 88.3526 | 81.036 | 67.6771 |

Figure 27:
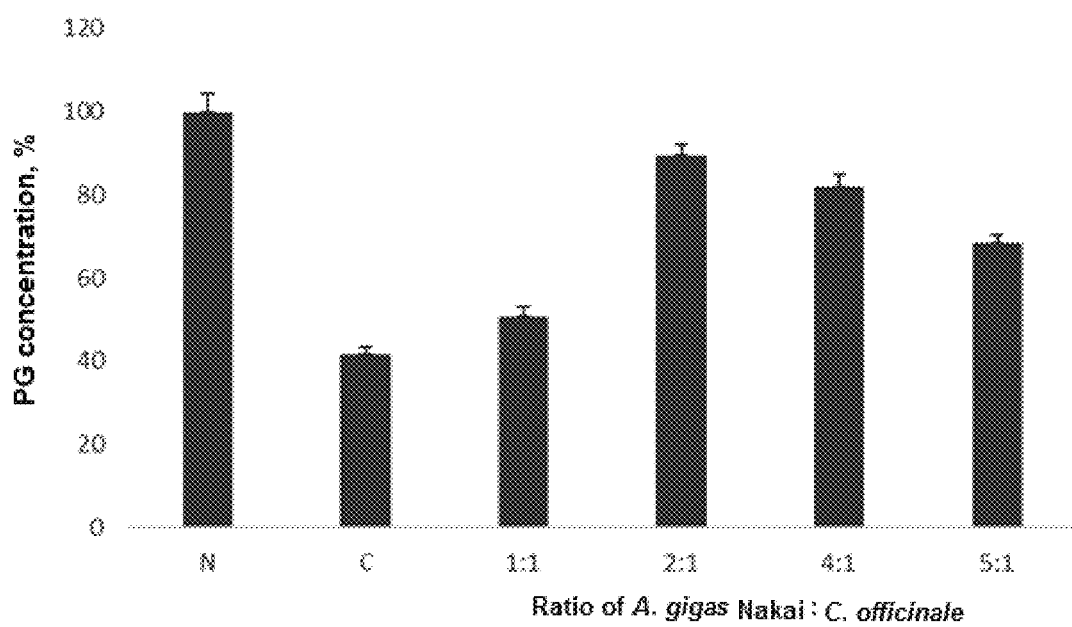
FIG. 27 is a graph showing changes in PG contents in the articular cartilages according to mixing ratios of the mixed extract of *Angelica gigas* Nakai and *Cnidium officinale*.

As shown in Table 10 and FIG. 27, 'N' represents the cartilage tissue of a normal white rat, and 'C' represents a white rat with MIA-induced osteoarthritis. As shown in Table 10 and FIG. 27, PG content ratios in the articular cartilage were significantly increased in the groups treated with a 1:1 mixed extract, a 2:1 mixed extract, a 4:1 mixed extract, and a 5:1 mixed extract (Example 1.3) of *Angelica gigas* Nakai and *Cnidium officinale*, compared with the non-extract-treated group after MIA injection. In particular, treatment of the 2:1 mixed extract, the 4:1 mixed extract, or the 5:1 mixed extract of *Angelica gigas* Nakai and *Cnidium officinale* showed higher PG content ratios in the articular cartilage than treatment of the 1:1 mixed extract of *Angelica gigas* Nakai and *Cnidium officinale*. The high PG content ratios in the articular cartilage indicate excellent inhibitory effect on PG destruction.

10.3. Effects of Ethanol Extract and Cold Ethanol Extract on PG Content in Articular Cartilage In the same manner as in Example 10.1, the PG destruction-inhibitory effects (measured by the PG content ratio in the articular cartilage tissue) of the ethanol extract of *Angelica gigas* Nakai (Example 1.1) and the mixed ethanol extract of *Angelica gigas* Nakai and *Cnidium officinale* (Example 1.3; a mixing ratio of 2:1) were tested, and compared with the water extract of *Angelica gigas* Nakai (Comparative Example 1), the cold ethanol extract of *Angelica gigas* Nakai (Comparative Example 3), the mixed water extract of *Angelica gigas* Nakai and *Cnidium officinale* (Comparative Example 2), and the mixed cold ethanol extract of *Angelica gigas* Nakai and *Cnidium officinale* (Comparative Example 4) (administration dose: 100 mg/kg).

The obtained results (PG content ratio in the articular cartilage tissue) are shown in the following Table 11 and FIG. 31.

Example 12: Comparison of Contents of Active Ingredients of *Angelica gigas* Nakai Extract According to Extraction Solvents 1

In order to compare the contents of active ingredients of the *Angelica gigas* Nakai extract according to extraction solvents, active ingredients of the ethanol extract of *Angelica gigas* Nakai prepared in Example 1.1 and the water extract of *Angelica gigas* Nakai prepared in Comparative Example 1 were analyzed as in Example 11.

The obtained results are shown in the following Table 12.

TABLE 11

|  | N | C | Water extract of *Angelica gigas* Nakai | Cold ethanol extract of *Angelica gigas* Nakai | Ethanol extract of *Angelica gigas* Nakai | Mixed water extract of *Angelica gigas* Nakai and *Cnidium officinale* | Mixed cold ethanol extract of *Angelica gigas* Nakai and *Cnidium officinale* | Mixed ethanol extract of *Angelica gigas* Nakai and *Cnidium officinale* |
|---|---|---|---|---|---|---|---|---|
| PG concentration, % | 100 | 40.6595 | 53.9079 | 62.7918 | 77.3418 | 59.8087 | 77.7684 | 85.7119 |

Figure 31:
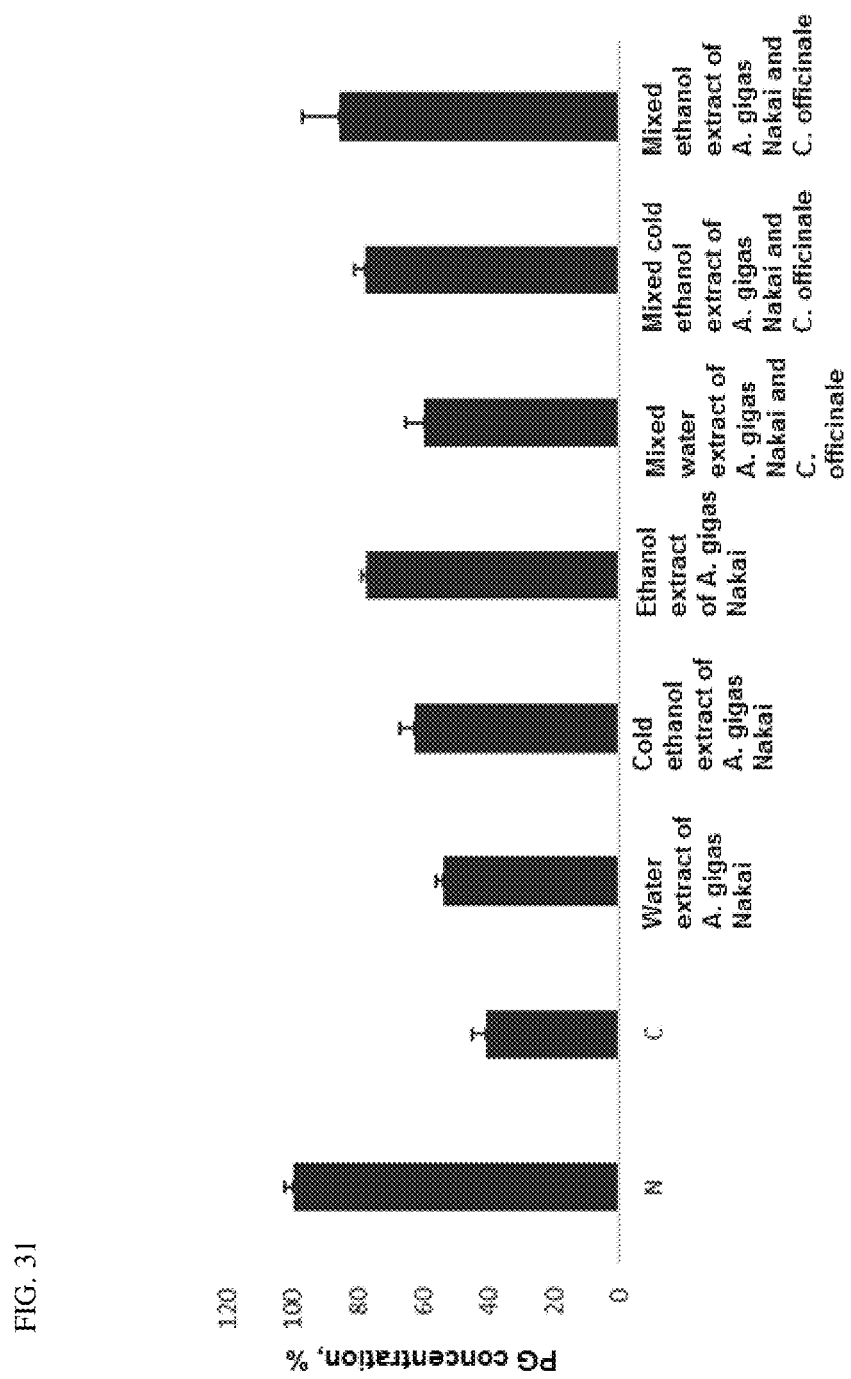
FIG. 31 is a graph showing changes in PG contents in the articular cartilages according to treatment of the ethanol extract or the cold ethanol extract.

In Table 11 and FIG. 31, 'N' represents the cartilage tissue of a normal white rat, and 'C' represents a white rat with MIA-induced osteoarthritis. As shown in Table 11 and FIG. 31, PG content ratios in the articular cartilage were remarkably increased in the group treated with the ethanol extract of *Angelica gigas* Nakai (Example 1.1) and the group treated with the mixed ethanol extract of *Angelica gigas* Nakai and *Cnidium officinale* (Example 1.3; a mixing ratio of 2:1), compared with the non-extract-treated group after MIA injection, and the groups treated with the water extract of *Angelica gigas* Nakai (Comparative Example 1), the cold ethanol extract of *Angelica gigas* Nakai (Comparative Example 3), the mixed water extract of *Angelica gigas* Nakai and *Cnidium officinale* (Comparative Example 2), and the mixed cold ethanol extract of *Angelica gigas* Nakai and *Cnidium officinale* (Comparative Example 4). These results indicate that the mixed extract of the above mixing ratio has excellent inhibitory effect on PG destruction.

Example 11: Composition and Content Analysis of *Angelica gigas* Nakai Extract About 150 mg of the ethanol extract powder of *Angelica gigas* Nakai prepared in Example 1 was taken and dissolved well in 100 mL of methanol, and then filtered using a 0.45 µm membrane filter to obtain a test liquid. 5 µL of the test liquid was injected into C18 HPLC and separated at a flow rate of 1.3 mL/min by isocratic elution of 50% acetonitrile solution (10 mM sodium lauryl sulfate, 25 mM disodium hydrogen phosphate, pH 5.0). Detection was monitored by UV at 230 nm.

Figure 15:
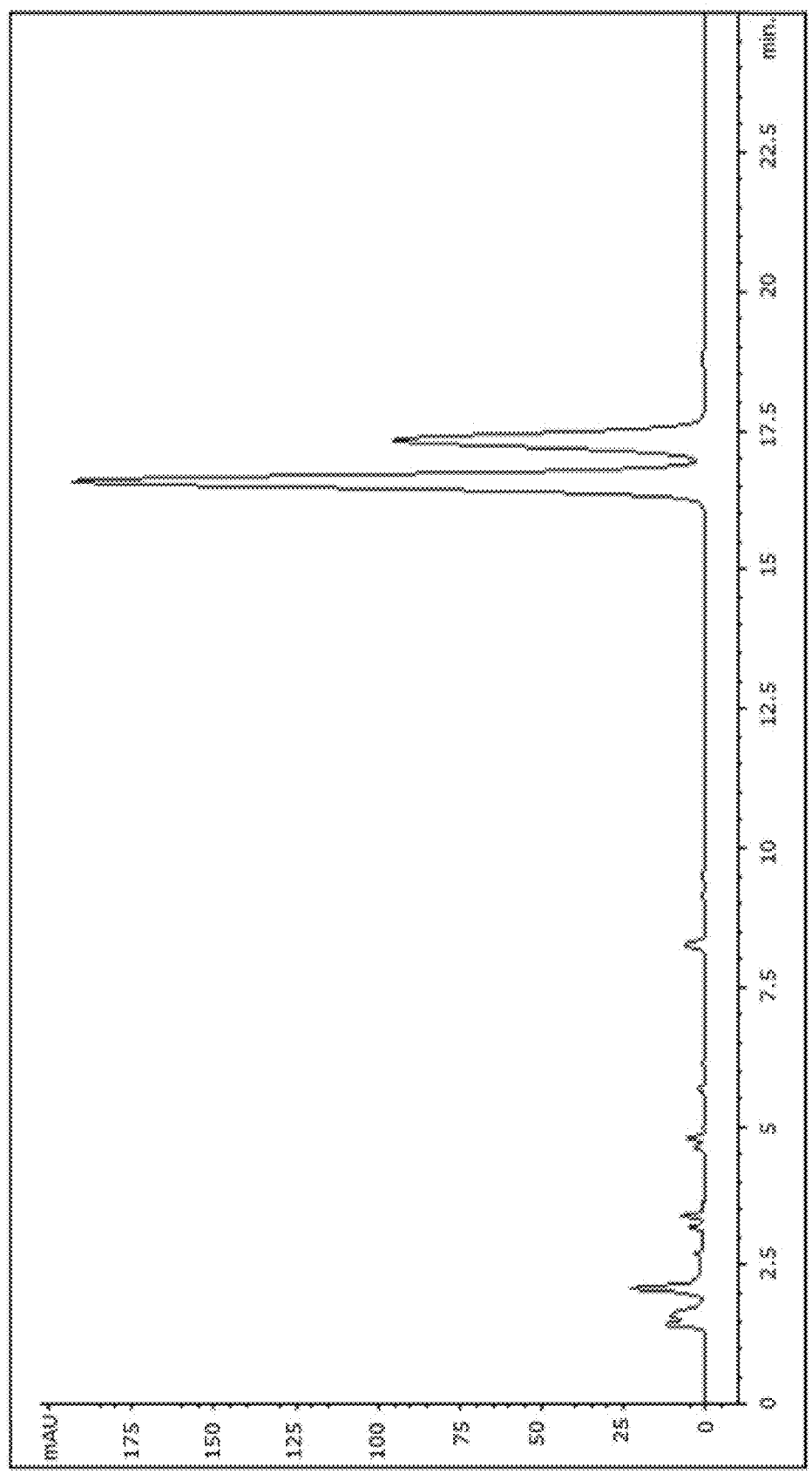
FIG. 15 is a graph showing the result of HPLC analysis of the *Angelica gigas* Nakai extract.

The obtained results are shown in FIG. 15. Decursin and decursinol angelate used as index components of *Angelica gigas* Nakai were eluted at 16.5 min and 17.2 min under HPLC conditions, respectively. A content of decursin in the ethanol extract powder sample of *Angelica gigas* Nakai prepared in Example 1 was 12.5±0.2% by weight of the total sample weight.

TABLE 12

| Extracts | Decursin (% by weight) |
|---|---|
| Hot water | 5.05% |
| Ethanol | 12.6% |

As shown in Table 12, the ethanol extract of *Angelica gigas* Nakai showed the content of decursin about 2.5 times higher than the hot water extract of *Angelica gigas* Nakai.

Example 13: Comparison of Contents of Active Ingredients of *Angelica gigas* Nakai Extract According to Extraction Solvents 2

13.1. Preparation of Extract 13.1.1. Preparation of Water Extract of *Angelica gigas* Nakai 500 ml of distilled water was added to 100 g of dried cut *Angelica gigas* Nakai, and extracted in a water bath (about 90° C.) for 8 hours. In the same manner, extraction was repeated four times, and the obtained liquids were combined, filtered, and concentrated in a rotary vacuum evaporator to prepare a water extract of *Angelica gigas* Nakai.

13.1.2. Preparation of Cold Ethanol Extract of *Angelica gigas* Nakai

About 150 g of *Angelica gigas* Nakai was pulverized using an herbal medicine grinder in a size of 100-200 mesh. To 100 g of the pulverized sample, about 1,000 ml (about 1:10 weight/volume) of 95% (v/v) ethanol was added, followed by extraction at room temperature for 5 days. Solids were removed using a Whatman filter paper NO. 4, and then concentrated using a rotary vacuum evaporator to prepare a cold ethanol extract of *Angelica gigas* Nakai.

13.1.3. Preparation of Ethanol Extract of *Angelica gigas* Nakai

The roots of *Angelica gigas* Nakai were washed with clean water, and then sufficiently dried, and pulverized using a grinder in a size of 100-200 mesh. To 100 g of the dried and pulverized powder of Angelica gigas Nakai, 500 ml of ethanol (95%) was added and extracted at 40° C.~50° C. for 4 hours or longer. A filtrate filtered through a 1 μm filter was concentrated in a rotary vacuum concentrator to about 10% of its original weight to prepare an ethanol extract of Angelica gigas Nakai (AGE232).

13.2. Component Analysis of Extract

The contents of decursin, decursinol, decursinol angelate, nodakenin, and β-sitosterol in each extract were analyzed by HPLC.

13.2.1. Analysis of Decursin and Decursinol Angelate

<Preparation of Test Liquid>

Each 1 g of three kinds of samples (water extract of Angelica gigas Nakai, cold ethanol extract of Angelica gigas Nakai, and ethanol extract of Angelica gigas Nakai (AGE232)) was accurately taken and added to a 50 ml measuring flask, and then dissolved with about 30 ml of methanol (100%). The flask was then filled to the mark with methanol, followed filtration. Each filtrate was used as a test liquid. The test liquids were prepared at different dilutions according to the kind of the sample and analysis items.

<Preparation of Standard Liquid>

5 mg of a standard decursin (purity of 98% or more) and 5 mg of a standard decursinol angelate (purity of 98% or more) were taken and each was added to a 25 ml flask, and then dissolved with 100% methanol. The flask was then filled to the mark with methanol and used as a standard liquid. From this standard liquid, standard solutions of 12.5-25-50-100-200 μg/ml were prepared, and used for measuring a calibration curve.

<HPLC Manipulation Conditions>

Liquid chromatography was performed under the following manipulation conditions using the test liquids and the standard liquids to calculate the contents of decursin and decursinol angelate.

Column: Cadenza CW C18, (150*4.6 mm, 3 μm) or an equivalent thereof

Detector: UV spectrophotometer (detection wavelength: 330 nm)

Flow rate: 0.7 ml/min

Mobile phase: Water (A %), Acetonitrile (B %)

0-5 min (20, B), 5-6 min (20→40, B), 6-22 min (40→55, B), 22-23 min (55→80, B), 23-25 min (80, B), 25-27 min (20, B)

Sample feeding: 10 μL (microliter)

13.2.2. Analysis of Nodakenin

<Preparation of Test Liquid>

Each 1 g of three kinds of samples (water extract of Angelica gigas Nakai, cold ethanol extract of Angelica gigas Nakai, and ethanol extract of Angelica gigas Nakai (AGE232)) was accurately taken and added to a 50 ml measuring flask, and then dissolved with about 30 ml of methanol (100%). The flask was then filled to the mark with methanol, followed by filtration. Each filtrate was used as a test liquid. The test liquids were prepared at different dilutions according to the kind of the sample and analysis items.

<Preparation of Standard Liquid>

Standard nodakenin (CAS Number: 495-31-8) (purity of 98% or more) was dissolved with methanol, and diluted at concentrations of 12.5-25-50-100-200 μg/ml to prepare a calibration curve.

<HPLC Manipulation Conditions>

Column: Cadenza CW C18, (150*4.6 mm, 3 μm) or an equivalent thereof

Detector: UV spectrophotometer (detection wavelength: 330 nm)

Flow rate: 0.7 ml/min

Mobile phase: Water (A %), Acetonitrile (B %)

0-5 min (20, B), 5-6 min (20→40, B), 6-22 min (40→55, B), 22-23 min (55→80, B), 23-25 min (80, B), 25-27 min (20, B)

Sample feeding: 10 μL 13.2.3. Analysis of Beta-Sitosterol

<Preparation of Test Liquid>

Each concentrated and dried sample was dissolved well with 100% methanol by sonication for 10-fold dilution. Microparticles were removed using a membrane filter before HPLC analysis.

<Preparation of Standard Liquid>

Standard beta-sitosterol (purity of 98% or more) was dissolved well with methanol by sonication, and diluted at concentrations of 12.5-25-50-100 μg/ml to prepare a calibration curve.

<HPLC Manipulation Conditions>

Column: Cadenza CW C18, (150*4.6 mm, 3 μm) or an equivalent thereof

Detector: UV spectrophotometer (detection wavelength: 205 nm)

Flow rate: 0.6 ml/min

Mobile phase: Water (A %), Acetonitrile (B %)

0-5 min (20, B), 5-6 min (20→40, B), 6-22 min (40→55, B), 22-23 min (55→80, B), 23-25 min (80, B), 25-27 min (20, B)

Sample feeding: 10 μL 13.2.4. Results

The obtained results of analyzing the components of each extract are shown in the following Table 13.

TABLE 13

Results of analyzing major components of Angelica gigas Nakai according to extraction solvent and extraction method

| Extraction Method | | Water extract | Cold ethanol extract | Ethanol extract (AGE232) |
|---|---|---|---|---|
| Ext. vol. before concent.(ml) | | 1,800 | 850 | 465 |
| Ext. weight after concent. (g) | | 42.0 | 14.2 | 30.5 |
| Total extracted compounds (mg) from 100 g of dried Angelica gigas Nakai | Decursin (mg) | 19 | 1920 | 3243 |
| | Decursinol angelate (mg) | 10 | 1130 | 1995 |
| | Nodakenin (mg) | 559 | 765 | 2982 |
| | β-Sitosterol (mg) | 13 | 25 | 324 |

As shown in Table 13, it was found that the ethanol extract of Angelica gigas Nakai 1) shows a remarkably excellent extraction efficiency, compared with the water extract of Angelica gigas Nakai and the cold ethanol extract of Angelica gigas Nakai, and 2) has the contents (based on the weight) of active ingredients such as decursin, decursinol angelate, nodakenin, and beta-sitosterol about 5 times to about 200 times (specifically, about 170 times (decursin), about 200 times (decursinol angelate), about 5 times (nodakenin), and about 25 times (beta-sitosterol)) higher than those of the water extract of Angelica gigas Nakai, and about 1.7 times to about 13 times (specifically, about 1.7 times (decursin), about 1.8 times (decursinol angelate), about 3.9 times (nodakenin), and about 13 times (beta-sitosterol)) higher than those of the cold ethanol extract of Angelica gigas Nakai.

What is claimed is:

1. A method of preventing or treating osteoarthritis, comprising administering an extract of *Angelica gigas* Nakai to a subject in need of prevention or treatment of osteoarthritis, wherein the extract of *Angelica gigas* Nakai is an ethanol extract of *Angelica gigas* Nakai comprising 2200 mg or more of decursin, 1400 mg or more of decursinol angelate, 1000 mg or more of nodakenin, and 50 mg or more of beta-sitosterol, based on 100 g of the extract, wherein the extract is obtained by extracting *Angelica gigas* Nakai with a 90% (v/v) to 100% (v/v) ethanol aqueous solution at 40° C. to 80° C.

2. The method of preventing or treating osteoarthritis of claim 1, wherein the ethanol aqueous solution has a concentration of 96% (v/v) to 100% (v/v).

3. A method of preventing or treating osteoarthritis, comprising administering a mixed extract of *Angelica gigas* Nakai and *Cnidium officinale* to a subject in need of prevention or treatment of osteoarthritis, wherein the mixed extract of *Angelica gigas* Nakai and *Cnidium officinale* comprises an extract of *Angelica gigas* Nakai and an extract of *Cnidium officinale*, and wherein the extract of *Angelica gigas* Nakai is an ethanol extract of *Angelica gigas* Nakai comprising 2200 MCl or more of decursin, 1400 mg or more of decursinol angelate, 1000 mg or more of nodakenin, and 50 mg or more of beta-sitosterol, based on 100 g of the extract, wherein the extract is obtained by extracting *Angelica gigas* Nakai with a 90% (v/v) to 100% (v/v) ethanol aqueous solution at 40° C. to 80° C., and the extract of *Cnidium officinale* is an ethanol extract of *Cnidium officinale* obtained by extracting *Cnidium officinale* with a 90% (v/v) to 100% (v/v) ethanol aqueous solution at 40° C. to 80° C.

4. The method of preventing or treating osteoarthritis of claim 3, wherein the ethanol aqueous solution used in the extraction of the ethanol extract of *Angelica gigas* Nakai, and the ethanol extract of *Cnidium officinale* has a concentration of 96% (v/v) to 100% (v/v).

5. The method of preventing or treating osteoarthritis of claim 3, wherein a mixing ratio between the extract of *Angelica gigas* Nakai and the extract of *Cnidium officinale* in the mixed extract is 2:1 to 5:1 (a weight of *Angelica gigas* Nakai:a weight of *Cnidium officinale*), based on a weight.

6. The method of preventing or treating osteoarthritis of claim 4, wherein a mixing ratio between the extract of *Angelica gigas* Nakai and the extract of *Cnidium officinale* in the mixed extract is 2:1 to 5:1 (a weight of *Angelica gigas* Nakai:a weight of *Cnidium officinale*), based on a weight.

* * * * *

SEQUENCE LISTING

<160> NUMBER OF SEQ ID NOS: 16

<210> SEQ ID NO 1
<211> LENGTH: 24
<212> TYPE: DNA
<213> ORGANISM: Artificial Sequence
<220> FEATURE:
<223> OTHER INFORMATION: iNOS forward primer

<400> SEQUENCE: 1
ttctttgctt ctgtgcttaa tgcg                                      24

<210> SEQ ID NO 2
<211> LENGTH: 23
<212> TYPE: DNA
<213> ORGANISM: Artificial Sequence
<220> FEATURE:
<223> OTHER INFORMATION: iNOS reverse primer

<400> SEQUENCE: 2
gttgttgctg aacttccaat cgt                                       23

<210> SEQ ID NO 3
<211> LENGTH: 21
<212> TYPE: DNA
<213> ORGANISM: Artificial Sequence
<220> FEATURE:
<223> OTHER INFORMATION: COX-2 forward primer

<400> SEQUENCE: 3
ctgcatgtgg ctgatgtcat c                                         21

<210> SEQ ID NO 4
<211> LENGTH: 25
<212> TYPE: DNA
<213> ORGANISM: Artificial Sequence
<220> FEATURE:
<223> OTHER INFORMATION: COX-2 Reverse primer

<400> SEQUENCE: 4
aggacccgtc atctccaggg taatc                                     25

<210> SEQ ID NO 5
<211> LENGTH: 20
<212> TYPE: DNA
<213> ORGANISM: Artificial Sequence
<220> FEATURE:
<223> OTHER INFORMATION: TNF-alpha Forward primer

<400> SEQUENCE: 5
gtagcccacg tcgtagcaaa                                           20

<210> SEQ ID NO 6
<211> LENGTH: 20
<212> TYPE: DNA
<213> ORGANISM: Artificial Sequence
<220> FEATURE:
<223> OTHER INFORMATION: TNF-alpha Reverse primer

<400> SEQUENCE: 6
cccttctcca gctggaagac                                           20

<210> SEQ ID NO 7
<211> LENGTH: 20
<212> TYPE: DNA
<213> ORGANISM: Artificial Sequence

```
<220> FEATURE:
<223> OTHER INFORMATION: 1L-1beta Forward primer

<400> SEQUENCE: 7
tgatgttccc attagacagc                                                  20

<210> SEQ ID NO 8
<211> LENGTH: 20
<212> TYPE: DNA
<213> ORGANISM: Artificial Sequence
<220> FEATURE:
<223> OTHER INFORMATION: 1L-1beta Reverse primer

<400> SEQUENCE: 8
gaggtgctga tgtaccagtt                                                  20

<210> SEQ ID NO 9
<211> LENGTH: 19
<212> TYPE: DNA
<213> ORGANISM: Artificial Sequence
<220> FEATURE:
<223> OTHER INFORMATION: 1L-10 Forward primer

<400> SEQUENCE: 9
cagtcagcca gacccacat                                                   19

<210> SEQ ID NO 10
<211> LENGTH: 18
<212> TYPE: DNA
<213> ORGANISM: Artificial Sequence
<220> FEATURE:
<223> OTHER INFORMATION: 1L-10 Reverse primer

<400> SEQUENCE: 10
gctccactgc cttgcttt                                                    18

<210> SEQ ID NO 11
<211> LENGTH: 24
<212> TYPE: DNA
<213> ORGANISM: Artificial Sequence
<220> FEATURE:
<223> OTHER INFORMATION: beta-actin Forward primer

<400> SEQUENCE: 11
ttgtaaccaa ctgggacgat atgg                                             24

<210> SEQ ID NO 12
<211> LENGTH: 23
<212> TYPE: DNA
<213> ORGANISM: Artificial Sequence
<220> FEATURE:
<223> OTHER INFORMATION: beta-actin Reverse primer

<400> SEQUENCE: 12
gatcttgatc ttcatggtgc tag                                              23

<210> SEQ ID NO 13
<211> LENGTH: 22
<212> TYPE: DNA
<213> ORGANISM: Artificial Sequence
<220> FEATURE:
<223> OTHER INFORMATION: MMP-3 Forward primer

<400> SEQUENCE: 13
gagtgtggat tctgccattg ag                                               22
```

```
<210> SEQ ID NO 14
<211> LENGTH: 24
<212> TYPE: DNA
<213> ORGANISM: Artificial Sequence
<220> FEATURE:
<223> OTHER INFORMATION: MMP-3 Reverse primer

<400> SEQUENCE: 14
ttatgtcagc ctctccttca gaga                                          24

<210> SEQ ID NO 15
<211> LENGTH: 24
<212> TYPE: DNA
<213> ORGANISM: Artificial Sequence
<220> FEATURE:
<223> OTHER INFORMATION: MMP-13 Forward primer

<400> SEQUENCE: 15
acgttcaagg aatccagtct ctct                                          24

<210> SEQ ID NO 16
<211> LENGTH: 21
<212> TYPE: DNA
<213> ORGANISM: Artificial Sequence
<220> FEATURE:
<223> OTHER INFORMATION: MMP-13 Reevrse primer

<400> SEQUENCE: 16
ggatagggct gggtcacact t                                             21
```